(12) United States Patent
Horton

(10) Patent No.: US 6,900,019 B1
(45) Date of Patent: May 31, 2005

(54) IN-SITU CELL EXTRACTION AND ASSAY METHOD

(75) Inventor: Jeffrey Kenneth Horton, Cardiff (GB)

(73) Assignee: Amersham Biosciences UK Limited, Buckinghamshire (GB)

( * ) Notice: Subject to any disclaimer, the term of this patent is extended or adjusted under 35 U.S.C. 154(b) by 0 days.

(21) Appl. No.: 09/027,654

(22) Filed: Feb. 23, 1998

(30) Foreign Application Priority Data

Mar. 3, 1997 (EP) .............................................. 97301398
Jul. 24, 1997 (GB) .............................................. 9715704

(51) Int. Cl.[7] ........................ G01N 33/53; G01N 33/543
(52) U.S. Cl. ........................ 435/7.1; 435/7.2; 435/7.8; 435/7.9; 435/174; 435/180; 436/501; 436/518; 436/523; 436/524; 436/533; 436/534; 436/536
(58) Field of Search ..................... 436/17, 518, 529, 436/533, 535, 538, 539, 541, 542, 545, 501, 523, 524, 534, 536; 435/4, 8, 39, 259, 91.2, 810, 7.1, 7.2, 7.8, 7.9, 174, 180

(56) References Cited

U.S. PATENT DOCUMENTS

| | | | |
|---|---|---|---|
| 4,303,752 A | | 12/1981 | Kolehmainen et al. ......... 435/8 |
| 4,568,649 A | | 2/1986 | Bertoglio-Matte .......... 436/534 |
| 5,032,503 A | * | 7/1991 | Khanna et al. ............. 435/7.6 |
| 5,185,432 A | | 2/1993 | Hellstrom et al. ....... 530/388.8 |
| 5,268,299 A | | 12/1993 | Shih et al. .................... 436/18 |
| 5,558,986 A | | 9/1996 | Lundin ........................... 435/4 |
| 5,705,345 A | * | 1/1998 | Lundin et al. .................. 435/6 |
| 5,739,001 A | | 4/1998 | Brown et al. .............. 435/7.93 |
| 6,159,750 A | * | 12/2000 | Edmonds .................... 436/537 |

FOREIGN PATENT DOCUMENTS

| | | |
|---|---|---|
| EP | 0 286 367 A2 | 10/1988 |
| EP | 0 301 847 A1 | 2/1989 |
| EP | 0 309 184 A2 | 3/1989 |
| EP | 0 348 173 A2 | 12/1989 |
| WO | WO 90/03844 | 4/1990 |
| WO | WO 92/12253 | 7/1992 |
| WO | WO 92/26413 | 11/1994 |

OTHER PUBLICATIONS

Baxendale, P.M. et al., *Advances in Prostaglandins, Thromboxane and Leukotriene Research*, 21, pp. 303–306 (1990) (Eds. Samuelsson, B. et al., Raven Press).

Cook, N.D., *Drug Discovery Today*, 1, 287–294 (1996).

Fiet, J. et al., *Clin. Chem.*, 37, 293 (1991).

Goldberg N.D. & O'Toole, A.G., *Methods of Biochemical Analysis*, 20, Ed Glick D., pp. 1–39 Interscience Publishers, Wiley, London (1971).

Hancock et al., *J. of Receptor & Signal Transduction Research*, 15, 557–579 (1995).

Heath R. Bryant B. & Horton J.K., The Biology of Nitric Oxide, Part 2, *Enzymology, Biochemistry and Immunology*, pp. 98–102 (1992) (Eds. Moncada S. et al., Portland Press).

Henderson, D.R. et al., Clin. Chem. 32, 1637–1641 (1986).

Horton, J.K. & Baxendale, P.M., *Methods in Molecular Biology*, 41, pp. 91–105 (1995) (Eds. Kendall, D.A. and Hill, S.J., Humana Press Inc., Towota, NJ).

Linacre, P. & Morris, S.E., *Bioanalytical Approaches for Drugs, including anti–asthmatics and metabolites*, 22, pp. 325–326 (1992) (Eds. Reid, E. & Wilson, I.D., Royal Society of Chemistry, London).

Rubenstein, K.E. et al., *Biochem. Biophys. Res. Comm.*, 47, 846 (1972).

Steiner, *Methods of Hormone Radioimmunoassay*, pp. 3–17 (1979) (Eds. Jaffre, B.M. & Behrman, H.R., Academic Press, New York).

Sugatani, J. et al., *Life Sciences*, 46, 1443–1450 (1990).

Szejtli, J., Cyclodextrins in Diagnostics, *Kontakte [Darmstadt]* 1988 [1], 31–36.

Tadepalli, S.M., Topham, P.A. & Quinn, R.P., *Clin. Chem.*, 36, 1104(1990).

Whitford, P.N. & Croker, S.J., *Phytochemical Analysis*, 2, 134–136 (1991).

* cited by examiner

*Primary Examiner*—Chris Chin
*Assistant Examiner*—Gailene R. Gabel
(74) *Attorney, Agent, or Firm*—Marshall, Gerstein & Borun LLP

(57) ABSTRACT

This invention provides a simple and convenient, single stage, single vessel cell extraction and assay method which is suitable for the extraction and measurement of a range of different types of analyte which occur as cellular components. The invention also provides kits of reagents suitable for performing cellular extraction and measurement as a single stage, single vessel process.

16 Claims, 5 Drawing Sheets

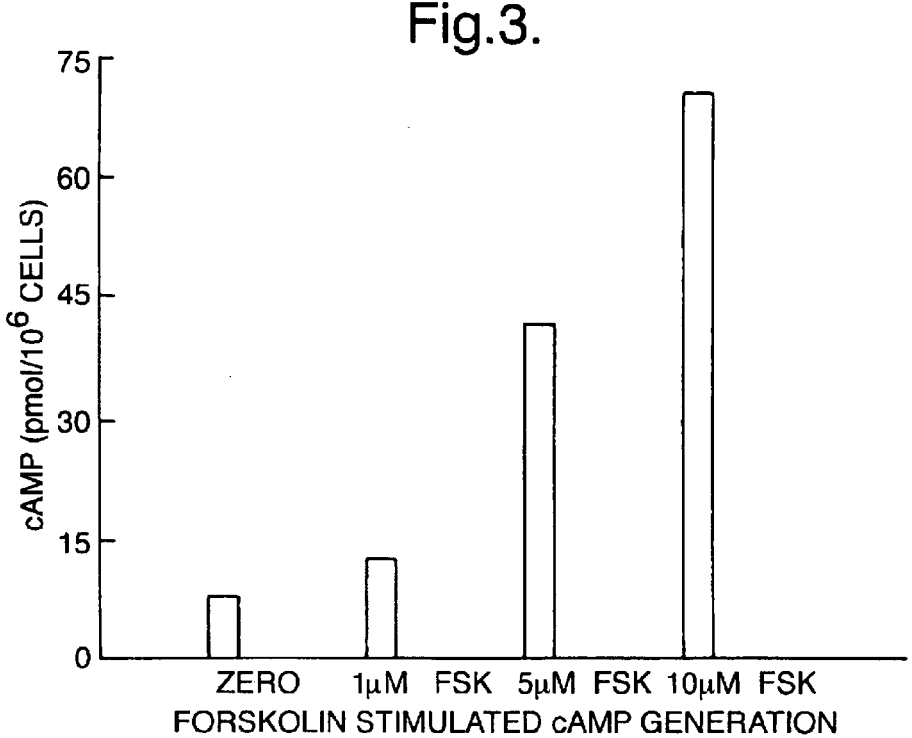
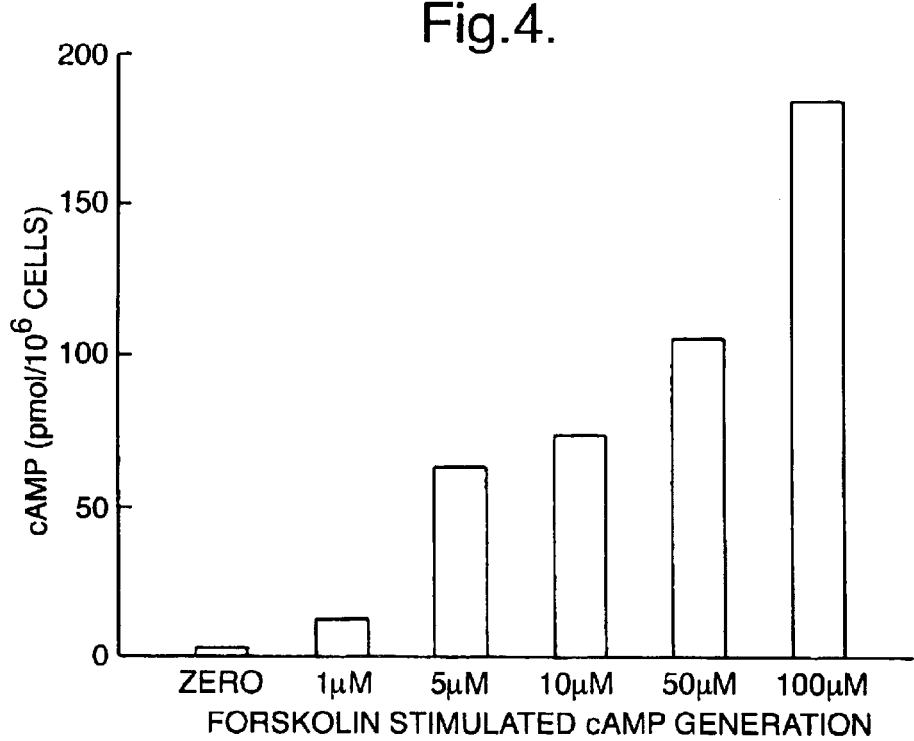

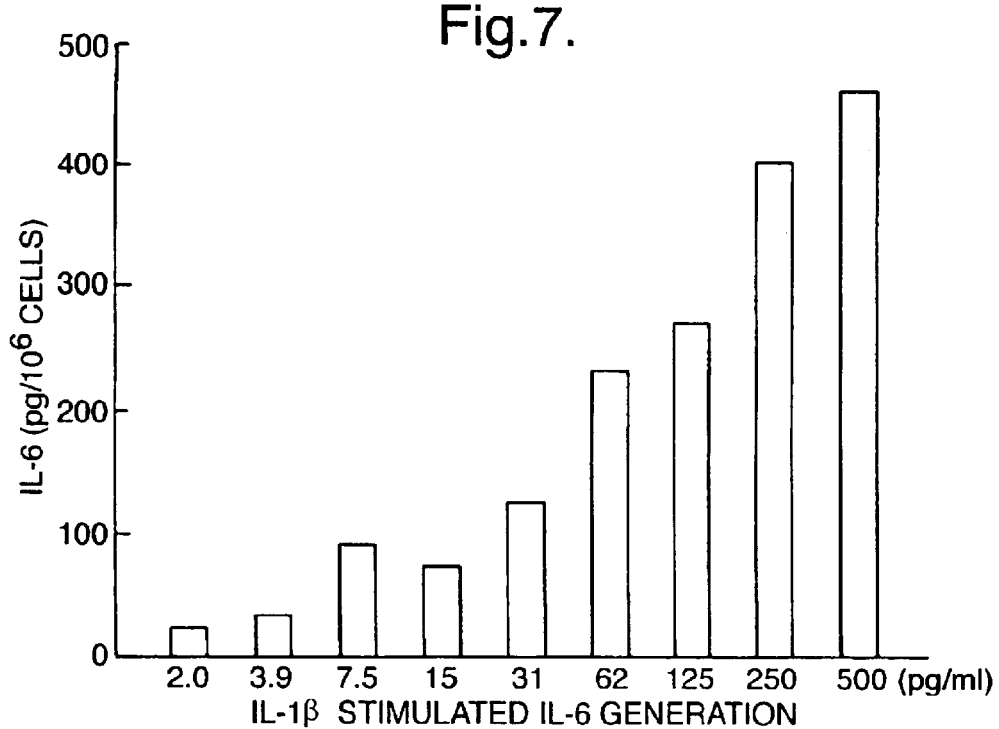
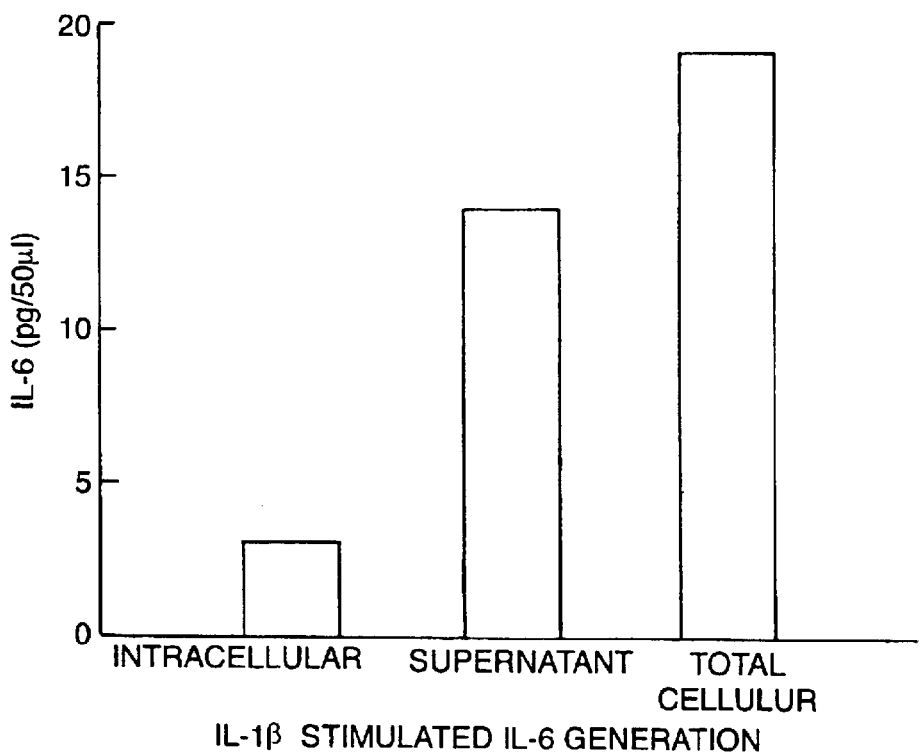

CM= CULTURE MEDIA ONLY (ZERO A23187)
DMS= CULTURE MEDIA PLUS DMSO (ZERO A23187)

IN-SITU CELL EXTRACTION AND ASSAY METHOD

FIELD OF THE INVENTION

The present invention relates to the field of immunoassays. The invention provides a simple and convenient, single stage, single vessel cell extraction and assay method which is suitable for the extraction and measurement of a range of different types of analyte which occur as cellular components. The invention also relates to kits of reagents suitable for performing cellular extraction and measurement as a single stage, single vessel process.

BACKGROUND TO THE INVENTION

1. Immunoassay Technology

A number of techniques are known and have been described for the measurement of small quantities of biological materials. Of these techniques, the area of immunoassays has been extensively reviewed and the technique forms the basis of many commercially available assay kits.

For more than thirty years, immunoassay has been the method of choice for measuring low analyte concentrations in complex biological fluids. The procedure is equally applicable to the measurement of low molecular weight compounds such as drugs, steroids and the like, as well as large molecular weight compounds such as protein molecules. The technique combines sensitivity and specificity. Immunoassays are used in basic biological research to investigate the physiological and possible pathological role of a wide range of potent biologically active substances, including cyclic nucleotides, prostglandins, leukotrienes, growth factors, steroid hormones and cytokines. Such research often leads to the identification of new therapeutic agents. Immunoassays are often used in the pharmaceutical industry in many aspects of drug development processes. These range from drug screening, toxicological, pharmacological and pharmacokinetic studies, through to clinical trials. Immunoassays have had their greatest impact in the area of clinical diagnostic tests. The technique has been employed for many years in hospital clinical biochemistry laboratories to diagnose disease and metabolic disorders. The technique was introduced in 1959 by Berson & Yalow. (Yalow, R. S. and Berson S. A., Assay of plasma insulin in human subjects by immunologic methods, Nature, (1959), 184, 1684). The combination of a signal which could be detected and a protein molecule (an antibody) which binds specifically and avidly to the analyte of interest lies at the heart of all immunoassay procedures. Assay designs have proliferated over the last thirty years, as have the different types of signal reagents and detection systems. Sophisticated instruments with associated computer hardware have been developed with the aim of increasing sample throughput. Further background information relating to immunoassay techniques can be found in 'The Immunoassay Handbook, (Wild, D. G. Ed, Stockton Press, New York, (1994), which deals with many of the concepts associated with immunoassay technology which are pertinent to the present invention. It considers, for example, competitive (also termed 'labelled analyte' or 'limited reagent') and immunometric ('labelled antibody' or 'reagent excess') systems.

The earliest methods were those which involved a step of separating the bound analyte from the free, in order to be able to measure the amount of bound analyte. Various separation methods have been described, including charcoal absorption, ammonium sulphate precipitation, magnetic particles ('Amerlex™'), etc. More recently, solid supports have been utilised for immunoassay procedures, including the walls of microtitre well plates.

A more recent development has been the introduction of homogeneous radioimmunoassay technology, notably the technique of scintillation proximity assays (SPA) covered by U.S. Pat. No. 4,568,649. Scintillation proximity assay is a radioisotopic assay technique which has gained wide acceptance in recent years, and is applicable to radioimmunoassays, as well as to radio-receptor and enzyme assays. The technique relies on the observation that β-particles emitted from radioisotopes will travel only a limited distance in an aqueous environment (in the case of tritium β-particles, this is 1.5 $\mu$m), before the energy is dissipated. In SPA, the target of interest is immobilised to a small to microsphere containing scintillant. When a radioisotopically labelled molecule is brought into close proximity with the microsphere, O-particle energy is transferred effectively to the scintillant, thereby causing the emission of light. Labelled molecules which remain free in solution are undetected because they are too distant from the scintillant-containing microsphere. In a typical radioimmunoassay, the microsphere is coated with a capture moiety, such as protein, A, or secondary antibodies, such as donkey-anti rabbit, sheep-anti-mouse antibodies. A sample, containing or suspected of containing the analyte (i.e. antigen) to be tested, is incubated in the presence of an antibody specific for that analyte, together with a quantity of a radiolabelled analyte. The antibody/analyte complex is captured by the secondary antibody and is detected by the emission of light. Any labelled antigen which remains unbound by the antibody, will be free in solution and be undetected. The assay therefore requires no separation step and the protocol has fewer pipetting steps compared with conventional, i.e. separation-based radioimmunoassays. It has been shown that in SPA-based assays, there is often an increase in assay precision and reproducibility, compared with traditional separation-based assays. Another advantage lies in the potential for increased sample throughput and capability for automation. (Cook, N. D., Drug Discovery Today (1996), 1, 287–294). The application of SPA to RIA methodology is not restricted to particular analytes or to types of molecule and in principle the technique can be applied in place of traditional separation-based assays. Some examples of RIAs developed using SPA are shown in Table 1.

TABLE 1

Examples of Radioimmunoassays Developed using SPA

| Assay | Reference |
| --- | --- |
| Cyclic AMP | Horton JK & Baxendale PM (1995), In: Methods in Molecular Biology, 41, pp. 91–105, Eds. Kendall, DA and Hill, SJ, Humana Press Inc, Towota, NJ |
| Cyclic GMP | Heath R Bryant B & Horton JK (1992), In: The Biology of Nitric Oxide. Part 2. Enzymology, Biochemistry and Immunology pp. 98–102, Eds. Moncada, S et al. Portland Press |
| 6-Keto-Prostoglandin F1 alpha | Baxendale PM et al (1990) In: Advances in Prostaglandins, Thromboxane and Leukotriene Research, 21, pp. 303–306, Eds. Samuelsson, B. et al, Raven Press |
| Acyclovir | Tadepalli, SM, Topham, PA & Quinn, RP. (1990) Clin. Chem. 36, 1104 |
| Platelet Activating Factor | Sugatani, J et al (1990), Life Sciences, 46, 1443–1450 |
| Abscisic Acid | Whitford, PN. & Croker, SJ. (1991) Phytochemical Analysis, 2, 134–136 |
| Androstenedione | Fiet, J. et al (1991) Clin. Chem., 37,293 |
| Ranitidine | Linacre, P. & Morris, SE, (1992), In: Bioanalytical Approaches for Drugs, including anti-asthmatics and metabolites, 22, pp.325–326 Eds. Reid, E. & Wilson, ID. Royal Society of Chemistry, London |

More recently, alternatives to scintillant-containing beads (fluomicrospheres) have been described for use in proximity assays. PCT Application No. WO 90/03844 (Wallac) discloses a microtitre well plate intended for binding assays. The sample plate is produced from a transparent scintillant-containing plastic by means of a vacuum thermoforming or injection moulding process. In principle, the walls of the microtitre well plate can be coated with a binding compound for the purpose of performing in vitro binding assays using radiolabelled reactants.

PCT Application No. WO 94/26413 discloses an apparatus and a method for studying cellular biochemical processes in real time. In one aspect, the application describes a multiwell plate, such as a microtitre well plate, in which the base of the plate is formed from a scintillant plastic material and the walls are formed from an opaque plastic material, the wells of the plate being adapted for the attachment or growth of cells. The scintillating microplates are designed for use in the real-time analysis of a wide spectrum of cell associated phenomena, and applications have been demonstrated in transport, cell motility, uptake, metabolism and other cell based processes. Cytostar™ scintillating microplates form the basis of a new technology introduced by Amersham International plc, for the study of cellular processes. In other applications, the scintillating microplates can be used for in vitro assays, for the measurement of ligands, analytes, etc. In this format a binding compound is bound to the walls of the microtitre well plate for reaction with label and analyte.

As an alternative to radioisotopic methods for performing immunoassays, non-radioactive systems have been introduced. Today, enzymes are the most widely used tracers. When in combination with colourimetric end-points, they provide highly sensitive, robust, precise, accurate and convenient immunoassays. A major breakthrough came with the introduction of ninety-six well microtitre plates. Inexpensive automatic colourimetric multiwell plate readers are available. A number of other non-isotopic labels have been described, of which luminescent and fluorescent labels are the most popular.

2. Cell Extraction Methods

Traditional methods for immunoassay depend on obtaining the samples in a sufficiently suitable state, i.e. sufficiently free from interfering factors. Usually this will involve a cellular extraction method. Numerous procedures are described which detail the extraction of intracellular molecules from cells. Typically these methods involve acid, solvent or solid phase methods to accomplish cell lysis and extraction of the molecule of interest. Methods for performing such extractions can be found in several publications. Further background information relating to cell extraction methods can be found in a review article by Goldberg & O'Toole. (Goldberg, N D & O'Toole, A G (1971); In: Methods of Biochemical Analysis, 20, Ed Glick D. pp 1–39 Interscience Publishers, Wiley, London)

Examples of cellular extraction methods are as follows.

2.1 Solvent Extraction (Horton & Baxendale, 1995; See Table 1 for Reference)

Ice-cold ethanol is added to cell cultures to give a final suspension volume of 65% (v/v) ethanol and the suspension allowed to settle. The supernatant is aspirated into test tubes, the remaining precipitate washed with ice-cold 65% (v/v) ethanol and the washings added to the appropriate tubes. The extracts are centrifuged at 2000 g for 15 minutes at 4° C. and the supernatant transferred to fresh tubes. The combined extract is then dried overnight, either under a stream of nitrogen at 60° C., in a vacuum oven for 8 hours, or in a centrifugal evaporator on a high temperature setting for 4 hours.

In this procedure, there is a possibility of overdrying, and this can result in difficulty in reconstituting the samples. The dried extracts are dissolved in a suitable volume of assay buffer before analysis.

2.2 Acid Extraction

Hancock et al, (J. of Receptor & Signal Transduction Research, 1995, 15, 557–579) describe an acid extraction method for intracellular molecules in which 0.2M hydrochloric acid is added to cells, and each separate sample is vortex mixed for 1–2 minutes. The sample is carefully neutralised to a pH that is compatible to the immunoassay, using stepwise addition of 10 µl aliquots of 2.5M sodium hydroxide, care being taken to measure the pH of the sample after each addition of alkali. This step is particularly critical, as the use of a non-optimal pH with an immunoassay can result in inaccurate measurement or non-measurement of analyte in the samples.

An alternative approach is described by Steiner, (In: Methods of Hormone Radioimmunoassay, 1979, Eds Jaffre, B M, & Behrman, H R pp. 3–17 Academic Press, New York), in which cell samples are homogenized in cold 6% (w/v) trichloroacetic acid at 4° C. to give a 10% (w/v) slurry. The sample is centrifuged at 2000 g for 15 minutes at 4° C. The supernatant is reserved and the pellet discarded. The supernatant is washed four times with five volumes of water-saturated diethyl ether, discarding the upper layer after each wash. The aqueous extract is lyophilized overnight or dried under a stream of nitrogen at 60° C. overnight and the dried extract dissolved in a suitable volume of assay buffer before analysis.

2.3 Solid Supports (e.g. Ion Exchange or 'Amprep' Columns)

A protocol for the extraction of intracellular molecules by ion exchange chromatography, using disposable minicolumns, has been described previously (Horton & Baxendale, 1995; see Table 1 for Reference). The columns (for example, ion exchange SAX columns) are used with a vacuum manifold and a vacuum pump. The columns are prepared by applying a vacuum and rinsing with 2 ml 100% methanol, followed by washing with 2 ml of water, taking careful precautions so as not to allow the solid support to dry, or to allow the flow rate to exceed 5 ml/minute. The cultured cells are applied directly to the column and washed with 3 ml 100% methanol. Three milliliters of acidified methanol (prepared by diluting concentrated hydrochloric acid to 0.1M with absolute methanol) is added to the column and the eluate collected. The fractions are dried using a stream of nitrogen or in a vacuum oven overnight (see above). The samples are reconstituted in assay buffer, as described above, before assay.

2.4 Detergent Methods

Other methods are known for the extraction of nucleic acid samples and nucleotides such as ATP. For example, Lundin and Anson (PCT WO 92/12253) describe a method for extracting an intracellular component in which bacterial cells are lysed with a detergent which is subsequently neutralised by addition of a cyclodextrin. A cellular component (e.g. ATP, DNA or RNA) liberated is subsequently measured or processed using biochemical or molecular biology (non-immunoassay) techniques such as the firefly luciferase and polymerase chain reaction assays. No reference is made in this patent application to one-step assays, homogeneous immunoassays, including scintillation proximity assay methods, or separation based immunoassay techniques.

EP 0 309 184 (Lumac) describes a method for the extraction of ATP from a microorganism with an ATP releasing agent and contacting the resultant solution with a neutralising agent which acts substantially to eliminate the distorting effect the releasing agent on the subsequent ATP assay. In EP 0 309 184 the releasing agent is preferably a cationic surface active agent which is preferably contacted with a non-ionic surface active neutralising agent.

The use of cyclodextrins to remove surfactants from solutions and surfaces and surfaces has been described previously in European Patent Application EP 301 847 (P. Khanna and R. Dworschack). According to this patent application, surfactants can be removed and cleaned from solutions and containers used in biochemical reactions by immobilised cyclodextrins. EP 286367 (Khanna et al) describes cyclodextrins as neutralisers of surfactants used as storage stabilisers for enzymes which are used as tracers in enzyme immunoassays. In a review, various applications of cyclodextrins in biological and chemical reactions have been described. (J. Szejtli, Cyclodextrins in Diagnostics, Kontakte [Darmstadt] 1988 [1]. 31–36).

The use of cyclodextrins, to neutralise surfactants added as extractants to release intracellular molecules, in a simple, single-step extraction and measurement immunoassay system has not been described previously.

All of the above prior art methods for immunoassays suffer from a number of disadvantages, including:
i) Unable to process large numbers of cells samples
ii) Time consuming
iii) Labour intensive
iv) Prone to errors because of the large number of steps
v) The need to remove the cell extraction reagent before further processing and measuring can take place. If this is not carried out, then accurate measurements may not take place, or, indeed, could result in total assay inhibition, and therefore measurement of the substance in the cellular extract is prevented.

In all of the traditional methods of sample preparation for radioimmunoassay, it has hitherto been necessary to perform separate lysis and extraction processes in order to obtain samples in a suitable form for subsequent measurement. The prior art methods therefore involve three separate processes which must be carried out sequentially, thereby adding to the time and cost of each immunochemical assay. In addition none of the prior art methods for the assay of intracellular components would be amenable to high throughput screening methods which are necessary if large numbers of samples are required to be processed. In this specification, data is presented whereby addition of a cellular lysis reagent to an immunoassay system, results in inhibition of antigen:antibody binding; and the inclusion of complex carbohydrates, such as cyclodextrins, restores the antigen:antibody binding event. In the preferred embodiment of the invention, 1% DTAB (dodecyl trimethyl ammonium bromide) is employed as a cellular lysis reagent (which inhibits antigen:antibody binding) and 2.5% alpha cyclodextrin is used as a sequestration reagent restoring antigen:antibody binding. These reagents, together with homogeneous immunoassay techniques, have enabled, for the first time, the establishment of a concerted one stage, single pot, cellular lysis and immunoassay system for the accurate measurement of intracellular molecules.

Thus, a novel, convenient and rapid method for the extraction and quantitation of target molecules is described here, which permits the growth of cells, the extraction of intracellular components and the subsequent assay of such components to be carried out in the same vessel. The technique is simple to perform and can be carried out with little technical intervention. Since few manipulations are necessary, the procedure is fully amenable to robotic automation

BRIEF DESCRIPTION OF THE DRAWINGS

FIG. 3. Forskolin-stimulated cAMP generation from cultured Chinese Hamster Ovary Cells as determined by the one-pot extraction SPA radioimmunoassay method.

FIG. 4. "Total" cellular cAMP measurement from cultured Chinese hamster ovary cells.

FIG. 7. Intracellular measurement of IL-6 from IL-IP stimulated ECV304 cells.

FIG. 8. Interleukin-6 measurement from ECV304 cells.

DESCRIPTION OF THE INVENTION

Figure 1:
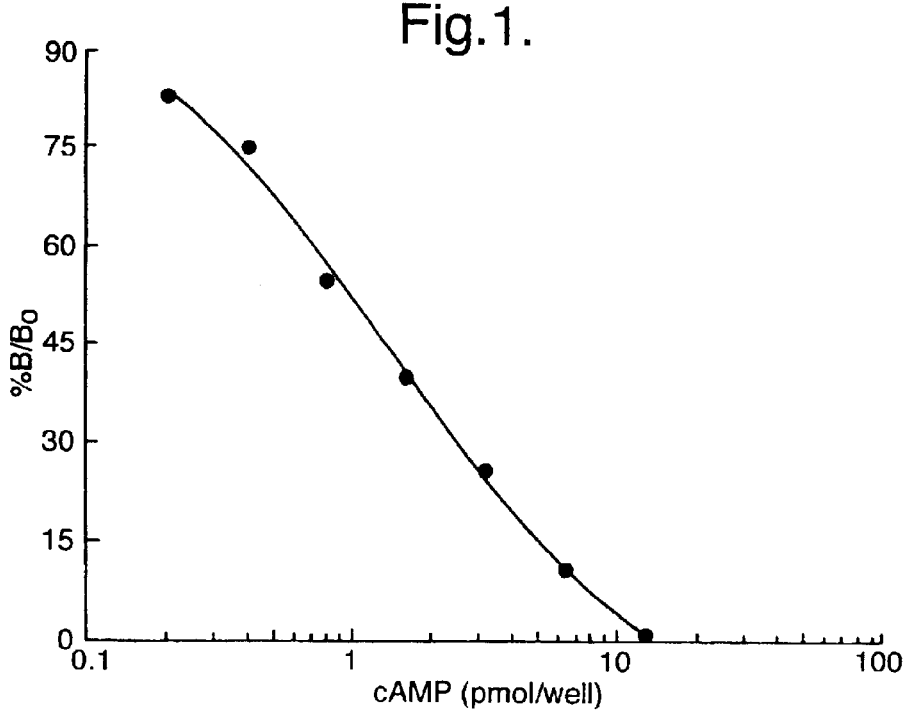
FIG. 1. Representative standard curve for the concerted one-pot extraction and immunoassay method for the estimation of adenosine 3'5' cyclic monophosphate from cultured Chinese Hamster Ovary cells. Assay curves were prepared on Viewplates (Packard) as described in the methods section.

The invention provides a method of assaying for an analyte which method comprises the steps of:
i) mixing a sample of cells possibly containing the analyte with a cell lysis reagent to provide a cell lysis fluid,
ii) mixing the cell lysis fluid with reagents, including a specific binding partner of the analyte for binding to the analyte, for performing a specific binding assay for the analyte,
iii) and mixing the cell lysis fluid with a sequestrant for the cell lysis reagent, whereby the binding of step ii) is performed in the presence of the sequestrant.

The analyte is a cellular component. Any cellular component for which a specific binding partner is available can in principle be utilised in the invention. Typical specific-binding partner combinations suitable for use with the invention may be selected from: hapten-antibody, ligand-receptor, DNA-DNA, RNA-RNA, DNA-RNA, biotin-streptavidin, protein-antibody, peptide-antibody, and polypeptide-antibody interactions. Preferably the specific binding assay is a protein-binding assay or particularly an immunoassay. Preferred cellular components include proteins, peptides, second messengers such as cyclic AMP and cyclic GMP, hormones, steroids, peptides, prostaglandins, inositol phosphates, cytokines chemokines and leukotrienes.

The assay may be designed to measure an analyte present within the cells, in which case the cells will usually be separated from a cell culture medium prior to lysis. Or the assay may be designed to measure an analyte present in both intracellular and extracellular fluids, in which case the cells will usually be lysed in the presence of a medium in which they have been cultured.

The cell lysis reagent is preferably a detergent, that is to say a surface active agent which may be cationic, anionic, zwitterionic or non-ionic. Examples of suitable detergents include dodecyl trimethyl ammonium bromide (DTAB); cetyl pyridinium chloride (CPC); benzethonium chloride (BZC); sodium dodecyl sulphate (SDS), and N-dodecyl-N, N-dimethyl-3-ammonio-1-propane sulphonate (DDAPS). DTAB, CPC and BZC are cationic surfactants; DDAPS is a zwitterionic surfactant and SDS is an anionic surfactant. The use of these detergents as cell lysis agents is well known in the field. Typical concentrations are in the range of 0.4–4% by weight on the weight of the cell lysis fluid. If too little detergent is used, then cell lysis may be slow or incomplete. In addition to lysing cells in order to release an intracellular component into a cell lysis fluid, the detergent may also adversely affect the binding of that intracellular component to its specific binding partner added in the course of step ii) for assay. The sequestrant is used to inhibit or annul that undesired adverse effect.

A key feature of the invention is the use of a sequestrant for the cell lysis reagent. The sequestrant acts to prevent the cell lysis reagent from adversely affecting a binding reaction between the analyte and its specific binding partner. The sequestrant may do this e.g. by chemically reacting with the cell lysis reagent or by physically absorbing it. Preferred sequestrants are carbohydrates such as cyclodextrins. Cyclodextrins are toroidal molecules consisting of 6, 7 or 8 glucose units ($\alpha$-, $\beta$- and $\gamma$-cyclodextrin). The interior of the ring binds a hydrophobic tail of a molecule such as a surfactant. The resultant inclusion complex is generally formed with a 1:1 stoichiometry between surfactant and cyclodextrin. $\gamma$-Cyclodextrin and particularly $\alpha$-cyclodextrin are preferred for use in this invention. Preferably enough sequestrant is used to be capable of sequestering or inactivating all the cell lysis reagent present. Preferably the amount of sequestrant is from 0.5–10%, particularly 1–5%, by weight on the weight of the reaction mixture.

Clearly, the method described herein can be readily adapted for use with traditional separation, non-homogeneous immunoassays, and also two-stage methods whereby cells are cultured in separate vessels from those used to carry out the immunoassay measurements.

It is an advantage of the invention that steps i), ii) and iii) can all preferably be performed in a single reaction vessel. The cells from which the analyte is extracted in step i) may be dead but are preferably living. It may be convenient to culture the cells in the reaction vessel in which the assay is to be performed. Preferably multiple assays are performed in parallel in wells of a multiwell plate such as a microtitre plate. If desired, the contents of individual wells of a multiwell plate can be transferred to individual wells of another multiwell plate at any stage during performance of the method.

Preferably the cell lysis fluid that results from step i) is used, without any intermediate separation or purification, for performing steps ii) and iii). Preferably the sequestrant is included in one of the reagents that is mixed with the cell lysis fluid in step ii). Thus the components present in an assay according to the invention may typically comprise:
a) a source of cells possibly, or suspected of, containing the analyte;
b) a cell lysis reagent;
c) an unlabelled specific binding partner of the analyte which is, or is capable of being, immobilised on a solid support;
d) a specific binding partner, or an analogue, of the analyte, which is either labelled or unlabelled and capable of being labelled.

One or both of components c) and d) includes a sequestrant, the order of addition of components c) and d) being immaterial.

In one format of the invention, the immunoassay is a scintillation proximity assay. In this format, components a), b), c) and d) are contained in the wells of a microtitre well plate, component d) being a radioactively labelled analogue of the compound being tested for. The scintillation proximity assay measurement is initiated by the addition to the wells of SPA fluomicrospheres coated with a binding reagent such as a secondary antibody or protein A.

Alternatively, cells may be cultured in the wells of a scintillant microtitre well plate suitable for the purpose, the base and/or walls of the wells being coated with a binding reagent such as a secondary antibody or protein A. After a suitable time, the remaining assay components, b), c) and d) are added to the wells.

In a second format of the invention, the immunoassay is an enzyme-immunoassay. In this format, components a), b), c) and d) are contained in the wells of a microtitre well plate, component d) being an enzyme-labelled specific binding partner of the compound being tested for. The assay measurement is initiated by the addition to the wells of detection reagents suitable for the detection of the enzyme label.

Suitable sequestration reagents are chosen from the group consisting of complex carbohydrates, including cyclodextrins. In a preferred format, alpha-cyclodextrin is employed in the method of this invention.

The method comprises incubating cells with cell lysis buffer, adding to the mixture of lysed cells, the labelled specific binding partner for the substance, followed by addition of the unlabelled specific binding partner, both reagents being dissolved in a buffer containing sequestration agent, and measuring the signal generated by the labelled specific binding partner as a measure of the amount of substance or component, with the entire quantities of reagents present in the reaction vessel at the same time. The signal obtained may be compared with the signals obtained using a set of standard quantities of substance using a parallel procedure and generating a standard curve for the assay.

In another aspect the invention provides a kit, for assaying for an analyte by the method described, comprising: a detergent; a sequestrant for the detergent; a specific binding partner of the analyte; a tracer; and separation means for separating bound tracer from unbound tracer. The tracer is a labelled assay reagent, which might be the specific binding partner of the analyte or might be another assay reagent. Separation means envisaged include assay reagents which are immobilised e.g. on SPA beads or magnetic beads or on an inner surface of the assay vessel. The kit may also include an analyte standard and a buffer.

In one format, the immunoassay process is a radioimmunoassay, in which the labelled specific binding partner contains a radioisotope. Suitable radioisotopes for use in the assay method of the present invention include $\beta$-emitting isotopes such as tritium, and iodine-125, which emits Auger electrons.

In an alternative format, the immunoassay process is an enzyme-immunoassay, in which the labelled specific binding partner is, or can be, bound to an enzyme label. Typical enzyme labels suitable for use in the present invention are alkaline phosphatase, $\beta$-galactosidase, horseradish peroxidase, malate dehydrogenase and glucose-6-phosphate dehydrogenase. Horseradish peroxidase is a particularly preferred enzyme label for use in the enzyme immunoassay method according to the present invention.

In another format, the labelled specific binding partner can include a fluorescence label. Suitable fluorescent labels for use in the present invention may be selected from fluorescein, rhodamine and cyanine dyes.

The precise assay format, choice of specific binding partner, the detection label, and the nature of the substance to be tested for are not critical to the present invention. Rather, the invention relies on the unexpected observation that a precise measurement of intracellular components can be made without the separate extraction and/or purification procedures being performed on the cell samples which are inherent in, and characterise the prior art methods.

Illustrative of the immunoassay methods which can be utilised in the present invention are the following assay formats.

I) Radioactive Assays

Scintillation Proximity Assay Using Scintillant Beads

The method provides a simple, single-step lysis and measuring method for intracellular components. The immunoassay reagents (antisera, tracer, SPA beads) are added to the same wells which are used for growing cells. The process is carried out in single wells without further technical intervention. In this aspect of the invention there is a requirement for cultured cells grown in a suitable vessel. In a preferred form of the invention there is a requirement for a tissue-culture treated microtitre plate with opaque walls and a clear base, to allow microscopic inspection of the cells. A lysis reagent is added to the cultured cells, followed by labelled specific binding partner, unlabelled specific binding partner and second antibody derivatised scintillant beads prepared in buffer containing the sequestration agent. Standards are added to empty microtitre wells on the same plate. The plate is incubated for a suitable time period before counting on a β-scintillation counter. The concentration of analyte in the samples is determined by interpolation from a standard curve.

Alternatively, following the lysis event, a specific binding partner coupled to scintillant beads is incubated with the antigen, together with a second specific binding partner. The second binding partner is unlabelled and detection is through a third binding reagent which is labelled.

Alternatively, following the lysis event, the antigen/second specific binding partner complex is bound to the scintillant beads, the second specific binding partner being unlabelled and detection is through a third binding reagent which is labelled.

Scintillation Proximity Assays Using Scintillating Microtitre Plates

In an alternative for of the assay system described above, a Cytostar-T plate (or equivalent) is used. In a preferred embodiment of the invention, there is a requirement for a sterile, tissue-culture-treated scintillant microtitre plate with opaque walls and a clear base to allow microscopic inspection of the cells. In this method, the plate is pre-coated with specific or secondary antibodies. As above, this method provides a simple, single-step lysis and measuring method for intracellular components of cultured cells grown in the Cytostar-T plate (or equivalent). The immunoassay reagents (tracer, +/−antisera) are added to the same wells which are used for growing cells. A lysis reagent is added to the cultured cells, followed by tracer (or antisera depending on whether primary or secondary antibodies have been used to coat the plate) dissolved in buffer containing the sequestration reagent. Standards are added to empty wells on the same plate. The plate is incubated for a suitable time period before counting on a P-scintillation counter. The concentration of analyte in the sample is determined by interpolation from a standard curve.

II Enzyme Immunoassays

'EMIT' Type (Rubenstein K E. et al, 1972. Biochem. Biophys. Res. Comm. 47; 846)

The enzymes malate dehydrogenase and glucose-6-phosphate dehydrogenase have been used extensively in the homogeneous immunoassay exemplified by the EMIT (Enzyme Multiplied Immunoassay Technique) system. Both enzymes are monitored by the conversion of the cofactor NAD to $NADH_2$ in a spectrophotometer at 340 nm. In this assay system, the analyte competes with labelled antigen for antibody binding sites. The activity of the enzyme is modified when the antibody binds to the labelled antigen.

Cells are cultured in a sterile, clear tissue culture treated microtitre plate, lysed and then the other components of the homogeneous EMIT EIA are added dissolved in buffer containing the sequestration (cyclodextrin) agent. Optical density is measured and the concentration of analyte in the samples is determined by interpolation from a standard curve. Standards are added to empty wells of the same plate that are not used for growing cells.

'CEDIA' Type (Henderson D R et al 1986 Clin. Chem. 32, 1637–1641)

In the cloned enzyme donor immunoassay method, two inactive fragments of β-galactosidase have been synthesized by genetic engineering. The large fragment, the enzyme acceptor, contains 95% of the enzyme, and the small fragment, the enzyme donor, consists of the remaining 5%. On mixing, the two fragments aggregate into tetramers which have β-galactosidase enzyme activity. In this assay, antigen is conjugated to the enzyme donor in such a way that aggregation with the enzyme acceptor is blocked if antibody binds to antigen. In the presence of analyte, less conjugate is bound by antibody, and enzyme activity is stimulated. In the absence of analyte, antibody binding to the conjugate prevents formation of the active enzyme.

Cells are cultured in a sterile, clear tissue culture treated microtitre plate, lysed and then the other components of the homogeneous CEDIA (antibody, enzyme-donor/ligand conjugate, enzyme acceptor monomer) are added dissolved in buffer containing the sequestration (cyclodextrin) agent. Optical density is measured and the concentration of analyte in the samples is determined by interpolation from a standard curve. Standards are added to empty wells of the same plate that are not used for growing cells III Fluorescence Immunoassay Formats Fluorescence Polarization Fluorescence polarization is a technique used to distinguish from free analyte without the need for separation. In competitive assays, for small molecules, fluorescent-labelled antigens (e.g. using fluorescein, rhodamine or cyanine dye reagents) as tracer. At the signal generation and detection stage, a fluorimeter generates vertically polarized light at the excitation wavelength of the fluorophore.

The emitted light, at a lower wavelength because of Stokes' shift, is detected through a vertical polarizing filter. Because free tracer rotates at a very high speed, the emitted light is always in a different plane from the incident light, so the amount of light detected through the polarizing filter is minimal. However the tracer bound the much larger antibody molecule is restrained from rotating at such a high speed and the emitted light is in almost the same plane as the incident light. Cells are cultured in a sterile, clear tissue culture treated microtitre plate, lysed and then the other components of the homogeneous fluorescence assay (antibody, fluorescent-tagged antigen) are added dissolved in buffer containing the sequestration (cyclodextrin) agent. Fluorescence is measured and the concentration of analyte in the samples is determined by interpolation from a standard curve. Standards are added to empty wells of the same plate that are not used for growing cells.

Fluorescence Resonance Energy Transfer (FRET)

Different fluorophores often have different activation and emission spectra (see Table 2). However, the activation peak of one fluorophore may overlap with the emission peak of another fluorophore. if the second fluorophore is placed in the immediate vicinity of the first, quenching of the fluorescent emission takes place through transfer of energy. This principle has been used in FRET by coupling one fluorophore to antibody and another to antigen. Binding of the antigen to antibody leads to close proximity and subsequent quenching. An alternative system involves two populations of antibodies raised against the same antigen, labelled with two different fluorophores. Binding of the two antibodies gives rise to close proximity and then energy transfer between the two leading to quenching or reduction in fluorescence. Cells are cultured in a sterile, clear tissue culture treated microtitre plate, lysed and then the other components of the homogeneous fluorescence are added dissolved in buffer containing the sequestration (cyclodextrin) agent. Fluorescence is measured and the concentration of analyte in the samples is determined by interpolation from a standard curve. Standards are added to empty wells of the same plate that are not used for growing cells.

TABLE 2

The spectral properties of Cyanine Fluorescent Dyes

| Fluorophore | Activation (nm) | Emission (nm) |
|---|---|---|
| Cy2 | 489 | 506 |
| Cy3 | 550 | 570 |
| Cy3.5 | 581 | 596 |
| Cy5 | 649 | 670 |
| Cy5.5 | 675 | 694 |
| Cy7 | 743 | 767 |
| FluorX | 494 | 520 |

Time-Resolved Fluorescence

Background fluorescence is one of the main problems with the use of fluorescence immunoassay, and its presence can severely limit the use of these methods. However, background fluorescence present in most biological material has the short lifetime of a few nanoseconds. For fluorophores with long fluorescence lifetimes, it is possible to measure fluorescence at a time when virtually all the background fluorescence has disappeared. This is essentially the principle of time resolved fluorescence and this method can be used in combination with fluorescence energy transfer and fluorescence polarization techniques.

IV) Other Methods

The method described in this patent can be applied to other diverse homogeneous (non-separation) immunoassay techniques such as luminescence, nephelometry, latex agglutination assays and their variants.

EXAMPLES

A. Preliminary Experiments

Scintillation Proximity Radioimmunoassay for Adenosine 3'5' Cyclic Monophosphate General Assay Conditions Measurement of adenosine 3'5'cyclic monophosphate (cAMP) was selected as a model system for studying lysis and measurement of intracellular molecules. A number of potential extractants were selected from among various surfactants known to lyse and liberate contents from eukaryotic cells. These lysis reagents were used in a series of experiments in combination with sequestrating reagents in order to determine optimal reagents to be used. Standard curves for cAMP were prepared in lysis and sequestrating reagents. Parameters such as assay sensitivity, standard curve working range and antigen: antibody binding were used to establish the most suitable reagents and optimal concentrations for both lysis and sequestrating agent. Standard curves were prepared as follows.

All assays were carried out in microtitre plates compatible with a microtitre plate beta scintillation counter. Standards (50 µl; 0.2–12.8 pmol/well), antisera (50 µl; at 1:11000 dilution), tracer (50 ul; 10000–20000 cpm) are added to anti-rabbit coated SPA beads (50 µl; 20 mg/ml). Non-specific binding was determined in the absence of specific rabbit antisera. SPA anti-rabbit reagent is placed onto a magnetic stirrer to ensure a homogeneous suspension before pipetting. All wells contained a total volume of 200 µl. The plates were sealed and incubated at room temperature (15–30° C.) for 15–20 hours. The amount of [$^{125}$I]cAMP bound to the SPA fluomicrospheres was determined by counting in a microtitre plate beta scintillation counter for 2 minutes.

Experiments were set up with:— a) Working standards (4–256 pmol/ml; 0.2–12.8 pmol/well) were prepared in assay buffer (0.05M sodium acetate buffer containing 0.01% sodium azide) only (control) or assay buffer containing lysis reagent (e.g. DTAB, CPC or SDS; see experiment 1) at various concentrations.

b) Rabbit anti-cAMP sera prepared in assay buffer only (control) or assay buffer containing sequestrating agent at various concentrations depending on the experiment.

c) Radioactive tracer: adenosine 3' 5'-cyclic phosphoric acid 2'-O-succinyl-3-[$^{125}$I] iodotyrosine methyl ester prepared in assay buffer only (control) or assay buffer containing sequestrating agent at various concentrations depending on the experiment.

d) Donkey anti-rabbit IgG coupled to scintillation proximity fluomicrospheres prepared in assay buffer only (control) or assay buffer containing sequestrating agent at various concentrations depending on the experiment.

Experiment 1: Inhibition of Antigen and Antibody Binding by Several Lysis Reagents Method In these experiments, standard curves were prepared for cAMP using the SPA immunoassay technique, described above, where working standards of cAMP were prepared in several lysis reagents at 1% (w/v) or 2% (w/v) final concentration. The detergents investigated included dodecyl trimethyl ammonium bromide (DTAB; Sigma Chemical Co. D8638), benzethonium chloride (BZC; Aldrich; B470-8), cetyl pyridinium chloride (CPC; Sigma Chemical Co; C9002), sodium dodecyl sulphate (SDS, Sigma chemical Co; L4509) and N-dodecyl-N,N-dimethyl-3-ammonio-1-propanesulphonate (DDAPS; Sigma Chemical Co.; D4516).

Results

Table 3a). The effect of several lysis reagents on antibody:antigen binding (zero concentration of sequestrant). These data shown are counts per minute (cpm) obtained on a TopCount™ microplate scintillation counter. Efficiencies of other multihead beta counters vary is from this and may give different results. Non-specific binding (NSB) data was obtained in the absence of specific rabbit antisera.

| Standard (pmol cAMP/well) | Control (no lysis reagent) | 1% DTAB | 1% BZC | 1% CPC | 1% SDS | 1% DDAPS |
|---|---|---|---|---|---|---|
| NSB | 113 | 130 | 111 | 121 | 118 | 181 |
| Zero | 2674 | 1429 | 951 | 466 | 1149 | 1109 |
| 0.2 | 2068 | 1118 | 644 | 270 | 1052 | 969 |
| 0.4 | 1952 | 1098 | 501 | 239 | 973 | 849 |
| 0.8 | 1770 | 1088 | 473 | 232 | 913 | 725 |
| 1.6 | 1463 | 977 | 426 | 147 | 859 | 610 |
| 3.2 | 1193 | 860 | 261 | 125 | 837 | 425 |
| 6.4 | 862 | 649 | 16 | 103 | 640 | 311 |
| 12.8 | 458 | 440 | 6 | 80 | 394 | 204 |

Table 3b). The effect of increased concentrations of several lysis reagents on antibody: antigen binding. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control (No detergent) | 2% CPC | 2% BZC | 2% DTAB | 2% DDAPS |
|---|---|---|---|---|---|
| NSB | 117 | 133 | 117 | 145 | 129 |
| Zero | 2615 | 173 | 486 | 272 | 579 |
| 0.2 | 2100 | 133 | 308 | 231 | 416 |
| 0.4 | 1937 | 128 | 338 | 231 | 426 |
| 0.8 | 1786 | 108 | 222 | 201 | 429 |
| 1.6 | 1466 | 82 | 156 | 195 | 339 |
| 3.2 | 1202 | 77 | 143 | 179 | 303 |
| 6.4 | 867 | 73 | 96 | 170 | 215 |
| 12.8 | 459 | 50 | 70 | 93 | 109 |

Discussion

These data clearly demonstrates a significant reduction in antigen:antibody binding (cpm) where lysis reagents were included in the cAMP immunoassay.

Experiment 2. Restoration of Antigen and Antibody Binding with the Addition of Sequestrant (2.5% Alpha-Cyclodextrin).

Method

In these experiments, standard curves for cAMP were prepared using the SPA immunoassay technique described above, where working standards of cAMP were prepared in 1% (w/v), 1.5% (w/v) or 2% (w/v) lysis reagents (DTAB, SDS or CPC). The control consisted of no lysis reagent or cyclodextrin added. The effect including 2.5% (w/v) alpha-cyclodextrin (alpha-CD) (Sigma Chemical Co.; C4642) on antigen:antibody binding was investigated. Here, tracer, antisera and SPA beads were prepared in assay buffer containing 2.5% (w/v) alpha-CD. A second control tested the effect of 2.5% (w/v) alpha-CD on the standard curve without addition of lysis reagent.

Results

Table 4a). The effect of lysis reagent (1% DTAB) on antigen antibody binding with or without the addition of sequestrant. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control (No lysis reagent) | 1% DTAB | 2.5% CD only | 1% DTAB 2.5% CD |
|---|---|---|---|---|
| NSB | 186 | 182 | 155 | 140 |
| Zero | 3504 | 1586 | 3300 | 3361 |
| 0.2 | 3205 | 1575 | 2790 | 2931 |
| 0.4 | 2861 | 1573 | 2485 | 2638 |
| 0.8 | 2576 | 1305 | 1979 | 2228 |
| 1.6 | 1948 | 1097 | 1503 | 1724 |
| 3.2 | 1461 | 813 | 1058 | 1169 |
| 6.4 | 990 | 619 | 674 | 811 |
| 12.8 | 596 | 439 | 415 | 520 |

Table 4b). The effect of lysis reagent (1% SDS) on antigen:antibody binding with or without the addition of sequestrant. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control (No detergent) | 1% SDS | 2.5% cyclodextrin only | 1% SDS plus 2.5% cyclodextrin |
|---|---|---|---|---|
| NSB | 167 | 118 | 199 | 163 |
| Zero | 3147 | 1149 | 3145 | 3261 |
| 0.2 | 2335 | 1128 | 2358 | 2374 |
| 0.4 | 2179 | 1052 | 1979 | 2040 |
| 0.8 | 2080 | 973 | 1682 | 1851 |
| 1.6 | 1665 | 913 | 1499 | 1463 |
| 3.2 | 1269 | 859 | 1143 | 1100 |
| 6.4 | 857 | 640 | 754 | 813 |
| 12.8 | 411 | 394 | 383 | 416 |

Table 4c). The effect of lysis reagent (1 and 2% CPC) on antigen:antibody binding with or without the addition of sequestrant. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control (No detergent) | 1% CPC | 1% CPC 2.5% CD | 2% CPC | 2% CPC 2.5% CD |
|---|---|---|---|---|---|
| NSB | 118 | 121 | 115 | 134 | 121 |
| Zero | 2615 | 466 | 2122 | 173 | 779 |
| 0.2 | 2100 | 270 | 1650 | 133 | 455 |
| 0.4 | 1937 | 239 | 1534 | 128 | 431 |
| 0.8 | 1786 | 232 | 1541 | 108 | 360 |
| 1.6 | 1466 | 147 | 1269 | 82 | 329 |
| 3.2 | 1202 | 125 | 1017 | 77 | 206 |
| 6.4 | 867 | 103 | 735 | 73 | 139 |
| 12.8 | 459 | 80 | 393 | 50 | 79 |

Table 4d). The effect of several lysis reagents on antigen:antibody binding with or without the addition of sequestrant. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control | 1% DDAPS | 1% DDAPS 2.5% CD | 2% DDAPS | 2% DDAPS 2.5% CD | 2% DTAB | 2% DTAB 2.5% CD |
|---|---|---|---|---|---|---|---|
| NSB | 121 | 137 | 142 | 130 | 137 | 138 | 132 |
| Zero | 2989 | 906 | 2179 | 510 | 738 | 217 | 741 |
| 0.2 | 2453 | 762 | 1792 | 423 | 579 | 198 | 578 |
| 0.4 | 2279 | 719 | 1724 | 370 | 613 | 216 | 566 |
| 0.8 | 2072 | 689 | 1612 | 350 | 543 | 201 | 579 |
| 1.6 | 1734 | 559 | 1342 | 290 | 413 | 179 | 471 |
| 3.2 | 1346 | 446 | 1153 | 252 | 351 | 176 | 403 |
| 6.4 | 916 | 326 | 823 | 194 | 262 | 144 | 313 |
| 12.8 | 600 | 173 | 453 | 115 | 140 | 78 | 190 |

Table 4e). The effect of varying concentrations of alpha cyclodextrin on antibody:antigen binding in the presence of 1.5% lysis reagent. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control | 1.5% DTAB only | 1.5% DTAB 2.5% CD | 1.5% DTAB 3% CD |
|---|---|---|---|---|
| NSB | 239 | 237 | 177 | 165 |
| Zero | 4623 | 819 | 4430 | 4306 |
| 0.2 | 4165 | 799 | 4069 | 3855 |
| 0.4 | 3612 | 713 | 3559 | 3629 |
| 0.8 | 3257 | 688 | 3369 | 2966 |
| 1.6 | 2550 | 513 | 2510 | 2356 |
| 3.2 | 1951 | 426 | 1991 | 1662 |
| 6.4 | 1368 | 376 | 1341 | 1220 |
| 12.8 | 922 | 264 | 849 | 753 |

Discussion

These data clearly demonstrates a significant restoration in antigen:antibody binding (cpm) where lysis reagents were added to the cAMP standards and where tracer, antisera and SPA beads were prepared in sequestration agent. Alpha-CD only had little impact on the standard curve.

Experiment 3: The Optimal Concentration of Sequestrant Method

In this experiment, standard curves for cAMP were prepared using the SPA radioimmunoassay where working standards of cAMP were prepared in 1% (w/v) DTAB. The effect of including 1% (w/v), 2% (w/v), 2.5% (w/v) and 5% (w/v) alpha-cyclodextrin on antigen:antibody binding was investigated. Here, tracer, antisera and SPA beads were prepared in assay buffer containing alpha-CD at the above concentrations. The control consisted of no lysis or cyclodextrin added to the assay.

Results

Table 5). The effect of lysis reagent and varying concentrations of sequestrant antigen: antibody binding. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control | 1% DTAB only | 1% DTAB 1% CD | 1% DTAB 2% CD | 1% DTAB 2.5% CD | 1% DTAB 5% CD |
|---|---|---|---|---|---|---|
| NSB | 172 | 130 | 121 | 179 | 165 | 140 |
| Zero | 3315 | 1429 | 1914 | 3250 | 3460 | 2980 |
| 0.2 | 3182 | 1118 | 1478 | 2849 | 3056 | 2490 |
| 0.4 | 2732 | 1098 | 1305 | 2525 | 2674 | 2145 |
| 0.8 | 2318 | 1088 | 1138 | 2143 | 2246 | 1800 |
| 1.6 | 1839 | 977 | 920 | 1639 | 1706 | 1372 |
| 3.2 | 1360 | 860 | 685 | 1245 | 1175 | 997 |
| 6.4 | 882 | 649 | 421 | 878 | 853 | 649 |
| 12.8 | 610 | 440 | 179 | 515 | 506 | 421 |

Discussion

These data clearly demonstrates a significant restoration in antigen:antibody binding (cpm) where lysis reagents were added to the cAMP standards and where tracer, antisera and SPA beads were prepared in sequestration agent. 1% (w/v) and 2% (w/v) alpha-CD restored binding to a limited degree. 5% (w/v) alpha-CD was inhibitory. 2.5% (w/v) alpha-CD gave optimal results.

Experiment 4: The Optimal Sequestrant Method

In this experiment, standard curves for cAMP were prepared using the SPA immunoassay technique where working standards were prepared 1% (wt) lysis reagent (DTAB). The effect of including 2.5% (w/v) alpha-cyclodextrin (CD) 2.5% (w/v) beta-cyclodextrin (beta-CD) (Sigma is Chemical Co.; C4767) and 2.5% (w/v) gamma-cyclodextrin (gamma-CD) (Sigma Chemical Co.; 4892) on antigen:antibody binding was investigated. Here, tracer, antisera, and SPA beads were prepared in assay buffer containing the appropriate sequestration reagent. The control consisted of no lysis agent or cyclodextrin added to the assay.

Results

Table 6). The effect of adding different sequestrants on antigen:antibody binding. These data shown are counts per minute (cpm) obtained on a TopCount microplate scintillation counter. Efficiencies of other multihead beta counters vary from this and may give different results. Non-specific binding (NSB) data was obtained in the absence of specific rabbit antisera.

| Standards (pmol cAMP/well) | Control | 1% DTAB | 1% DTAB 2.5% alpha CD | 1% DTAB 2.5% beta CD | 1% DTAB 2.5% gamma CD |
|---|---|---|---|---|---|
| NSB | 212 | 130 | 173 | 103 | 172 |
| Zero | 4276 | 1429 | 4135 | 3225 | 4295 |
| 0.2 | 3752 | 1118 | 3604 | 2664 | 3650 |
| 0.4 | 3411 | 1098 | 3229 | 2360 | 3322 |
| 0.8 | 2788 | 1088 | 2548 | 1755 | 2270 |
| 1.6 | 2100 | 977 | 2005 | 1304 | 2066 |
| 3.2 | 1588 | 860 | 1480 | 966 | 1413 |
| 6.4 | 1104 | 649 | 1043 | 658 | 966 |
| 12.8 | 692 | 440 | 498 | 322 | 532 |

Discussion

The data demonstrates a significant restoration in antigen:antibody binding (cpm) where lysis agent was added to the cAMP standards, and where tracer, antisera and SPA beads were prepared in each of the sequestration reagents. Alpha and gamma cyclodextrin restored binding to an optimal degree, whereas beta-cyclodextrin was less effective.

Overall Conclusions

These preliminary experiments established the utility of dodecyl trimethyl ammonium bromide (DTAB) as the preferred surfactant for cell lysis.

Similarly, in preliminary experiments, several sequestration reagents were evaluated including alpha-cyclodextrin, beta-cyclodextrin and gamma-cyclodextrin. Alpha-cyclodextrin was established as the preferred sequestration reagent.

B. The Optimised Assay System

Example 1

Single-Step Extraction and Measurement of Adenosine 3'. 5' Cyclic Monophosphate from Forskolin-Stimulated Chinese Hamster Ovary Cells Reagents, Buffers and Equipment The following solutions were prepared:
1) Assay buffer; 0.05M sodium acetate buffer containing 0.01% (w/v) sodium azide.
2) Lysis reagent; DTAB (10% w/v) dissolved in assay buffer (useful for non-adherent cell lines).
3) Lysis reagent; DTAB (1% w/v) dissolved in assay buffer (useful for adherent cell lines such as Chinese Hamster Ovary Cells, this example).
4) Sequestration reagent; alpha-cyclodextrin (2.5% w/v) dissolved in assay buffer.
5) Adenosine 3', 5' cyclic monophosphate (cAMP) standard; 512 pmol, for the assay, used in the range 0.2–12.8 pmol/well, prepared in 2 ml of assay buffer containing 1%(w/v) DTAB to give 256 pmol/ml (see below).
6) Radioactive tracer: adenosine 3',5'-cyclic phosphoric acid 2'-O-succinyl-3-[$^{125}$I] iodotyrosine methyl ester prepared in assay buffer containing 2.5% alpha-cyclodextrin.
7) Rabbit anti-cAMP sera prepared in assay buffer containing 2.5% alpha-cyclodextrin.
8) Donkey anti-rabbit IgG coupled to scintillation proximity fluomicrospheres prepared in assay buffer containing 2.5% alpha-cyclodextrin.

Additional materials and equipment required are as follows.
i) Clear-bottomed microtitre plates with opaque walls, tissue culture treated plates (e.g. Viewplates™, Packard or Cytostar-T plates, Amersham).
ii) Microplate scintillation counter.
iii) Plate sealers.
iv) Disposable polypropylene or polystyrene test tubes for preparing working standards.
v) Pipettes and pipetting equipment.
vi) Laboratory glassware.
vii) Distilled water.
viii) Vortex mixer.
ix) Magnetic stirrer.
x) 1% (w/v) trypan blue solution prepared in water.
XI) Haemocytometer
XII) HAM's culture media
ix) Dimethylsulphoxide
iv) Forskolin
V) Cultured Chinese hamster ovary (CHO) cells at approximately $10^6$ cells/ml.

Method

Chinese hamster ovary cells were grown in HAM's media containing 10% (v/v) foetal calf serum (FCS). For cAMP assays, cells were seeded into 96-well tissue culture plates (see materials) in HAM's media, as above, at 100 µl/well ($10^5$ cells/well). The cells were cultured overnight at 37° C. in a 95% air/5% $CO_2$ atmosphere. The next day, sequestration and lysis buffers (2.5% alpha-cyclodextrin and 1% DTAB in assay buffer) were prepared. Antisera (at 1/11000 dilution), tracer (10000–20000 cpm) and SPA beads (20 mg/ml) were prepared in assay buffer containing 2.5% alpha-cyclodextrin. Working standards (4–256 pmol/ml; 0.2–12.8 pmol/microtitre well) were prepared in polypropylene tubes using assay buffer containing 1% DTAB. Fifty microliters aliquots of each working standard were added to empty of wells of the same microtitre plate used for culturing cells. Forskolin (1 mg) (to stimulate cAMP generation) was dissolved in DMSO (1 ml), and diluted with HAM's media containing 10% FCS, to give various concentrations of forskolin from 1 µM to 10 µM. Two assay controls (blanks) were prepared in a similar manner. These consisted of a DMSO (assay) blank and a culture media (sample) only blank. The forskolin and blank solutions (100 µl) were added to the cultured cells, and incubated at 37° C., as above, for 20 minutes. At this stage, a check was made that the cells remained viable using a trypan blue exclusion test. The culture media was aspirated from the stimulated walls (the cells remain adhered to the surface of the culture vessel), and the incubation terminated by the addition of lysis reagent (1% DTAB dissolved in assay buffer). A check for cell lysis was made with a second trypan blue exclusion test.

Fifty microliters of primary antibody, tracer, and SPA beads (prepared in buffer containing 2.5% (w/v) alpha CD), were added to standards and the samples in the 96-well culture plate. The plates were sealed and incubated overnight at room temperature. Following incubation, the plates were transferred directly to a TopCount™ scintillation counter and radioactivity detected. Non-specific binding was determined in the absence of specific rabbit antisera. Cyclic AMP levels were determined using-log/linear analysis with reference to the standard curve. Levels were estimated by interpolation.

This method is readily modified for extraction and measurement of cAMP in non-adherent cells (e.g. HL60 cells). For this modified procedure, 10% (w/v) lysis reagent (10% DTAB dissolved in assay buffer) is added to the cultured cells to give a final concentration of 1% (w/v). The remainder of the method is as described above.

Results

Dose-response curves were prepared for the one-step in situ measurement of cAMP from forskolin stimulated CHO cells. Representative standard curves prepared on Viewplates and Cytostar-T plates are shown FIGS. 1 and 2 respectively. In FIG. 3, the effect of 1, 5 or 10 µM forskolin on intracellular cAMP levels as measured by the one-step in situ measurement method on cells grown in 96-well plates is presented. CHO cells were seeded at a density of 100,000 cells/well and grown overnight in 96-well plates as described in the methods section. Cells were exposed to various concentrations of forskolin for 20 minutes and cAMP levels measured as described above. Basal levels of cAMP were approximately 10 pmol/$10^6$ cells in the absence of added forskolin and were augmented by the increasing concentrations of forskolin.

Discussion

These data illustrate the utility of the invention described in this patent application, whereby intracellular molecules are measured in a concerted one-pot lysis and estimating immunoassay system. Indeed, the data presented in FIG. 3 demonstrates lysis and measurement of cAMP in forskolin-stimulated Chinese Hamster Ovary cells. The estimated levels of this cyclic nucleotide is in accordance with other published data whereby cAMP was determined by a more complex procedure (see Hancock et al., 1995). Furthermore, we have accumulated results in separate experiments whereby cAMP levels were measured with the method described in this patent application and compared with levels extracted and subsequently estimated with a traditional procedure (ethanol extraction procedure, Horton & Baxendale, 1995) (data not shown). The results, obtained with these two different methods, gave highly similar values in levels of intracellular cAMP.

Example 2

Single-Step Extraction and Measurement of "Total" Cellular cAMP from Forskolin-Stimulated Chinese Hamster Ovary Cells This experiment describes the method for estimating levels of "total" cellular analyte. The procedure is applicable to cell culture systems and measures the intracellular fraction, and the component found in the cell culture supernatant. Accurate measurement of target analyte is achieved and the method has the advantage that aspiration or decantation of the cell culture media is not required. The technique is therefore useful for detection and measurement of molecules that are actively secreted into the extracellular fluid (see also Example 4).

Reagents, Buffers and Equipment

The following solutions were prepared.
1) Assay buffer; 0.05M sodium acetate buffer containing 0.01% (w/v) sodium azide.
2) Lysis reagent; DTAB (10% w/v) dissolved in assay buffer.
3) Lysis reagent; DTAB (1% w/v) dissolved in assay buffer.
4) Sequestration reagent; alpha-cyclodextrin (2.5% w/v) dissolved in assay buffer.
5) Adenosine 3',5'-cyclic monophosphate (cAMP) standard; 512 pmol (assay range, 0.2–12.8 pmol/well) prepared in 2 ml of assay buffer containing 1% (w/v) DTAB to give 256 pmol/ml (see method).
6) Radioactive tracer adenosine 3',5'-cyclic phosphoric acid 2'-O-succinyl-3-[$^{125}$I] iodotyrosine methyl ester prepared in assay buffer containing 2.5% (w/v) alpha-cyclodextrin.
7) Rabbit anti-cAMP sera prepared in assay buffer containing 2.5% (w/v) alpha-cyclodextrin.
8) Donkey anti-rabbit IgG coupled to scintillation proximity fluomicrospheres prepared in assay buffer containing 2.5% (w/v) alpha-cyclodextrin.

Additional materials and equipment required are as follows:
i) Clear-bottomed microtitre plates with opaque walls (tissue-culture treated) (e.g. Viewplates™, Packard or Cytostar-T plates, Amersham).
ii) Microplate scintillation counter.
iii) Plate sealers.
iv) Disposable polypropylene or polystyrene test tubes for preparing working standards.
v) Pipettes and pipetting equipment.
vi) Laboratory glassware.
vii) Distilled water.
viii) Vortex mixer.
ix) Magnetic stirrer.
x) 1% (w/v) trypan blue solution prepared in water.
xi) Haemocytometer
xii) HAM's culture media (Sigma; N4888)
xiii) Dimethylsulphoxide
xiv) Forskolin
xv) Cultured Chinese hamster ovary (CHO) cells at approximately $10^6$ cells/ml.

Method

Chinese hamster ovary (CHO) cells were cultured in HAM's media containing 10% (v/v) foetal calf serum (FCS). For cAMP assays, cells were seeded into clear-bottomed 96-well tissue-culture plates with opaque walls (tissue-culture grade; see materials) in HAM's media, (see experiment 5) at 40 µl/well (between $10^4$ and $10^6$ cells/well). Cells were cultured overnight at 37° C. in a 95% air/5% $CO_2$ atmosphere. The next day, sequestration and lysis buffers (2.5% alpha-cyclodextrin, 1% and 10% DTAB in assay buffer) were prepared. Antisera (at 1/11000 dilution), tracer (10000–20000 cpm) and SPA beads (20 mg/ml) were reconstituted with assay buffer containing 2.5% (w/v) alpha-cyclodextrin. Working standards (4–256 pmol/ml; 0.2–12.8 pmol/microtitre well) were prepared in polypropylene tubes, using assay buffer containing 1% DTAB. 50 µl of each working standard were added to empty wells of the microtitre plate used for culturing cells. Forskolin (1 mg) (to stimulate cAMP generation) was dissolved in DMSO (1 ml), and diluted with HAM's media containing 10% FCS, to give various concentrations of forskolin from 10 µM to 1000 µM (1 µM to 100 µM forskolin final concentration). To the cultured cells, 5 µl aliquots of agonist or cell stimulant (in this case forskolin) was added directly to the cultured cells. The cells were incubated for 20 minutes at room temperature. The culture media was not aspirated or decanted after incubation. Two assay controls (blanks) were prepared in a similar manner. These consisted of a DMSO (assay) blank and a culture media (sample) only blank. At this stage, a check was made using a cell viability (trypan blue exclusion) test. To the stimulated cells, 5 µl of cell lysis reagent (10% DTAB in assay buffer) was added. The final volume was 50 µl, each well containing 1% cell lysis reagent (final concentration). The cells were agitated after cell lysis reagent was added by vigorous, successive pipetting. The plate was incubated for 5 minutes at room temperature. Cell lysis was checked with a second trypan blue exclusion test. The extracted cAMP was immediately processed for measurement with the SPA radioimmunoassay. (In this example, aliquots were not transferred to a second plate for assay.)

DTAB (100 µl, 1% w/v in assay buffer) was added to the non-specific binding wells. DTAB (50 µl, 1% w/v in assay buffer) was added to the zero standard wells. 50 µl of each standard (prepared in assay buffer containing 1% DTAB) was added to the appropriate wells. 50 µl of primary antibody, tracer, and SPA beads (prepared in buffer containing 2.5% (w/v) alpha-cyclodextrin), were added to the standards and samples. The plate was sealed and incubated overnight at room temperature. Following incubation, the plate was transferred directly to a TopCount™ scintillation counter and radioactivity detected. Non-specific binding was determined in the absence of specific rabbit antisera. Cyclic AMP levels were determined using log/linear analysis with reference to the standard curve. Levels were estimated by interpolation.

This method is readily modified for extraction and measurement of cAMP in non-adherent cells (e.g. HL60 cells). For this modified procedure, 10% (w/v) lysis reagent (10% DTAB dissolved in assay buffer) was added to the cultured cells to give a final concentration of 1% (w/v). There was no centrifugation or decantation and aspiration steps to remove the cell culture supernatant. The remainder of the method is as described above.

Results

The effect of 1 µM to 100 µM forskolin on "total" cellular cAMP levels in cultured CHO cells, is presented in FIG. 4. In this experiment, CHO cells were seeded at a density of 100,000 cells/well and grown overnight in 96-well plates as described in the methods section. Cells were exposed to various concentrations of forskolin for 20 minutes and total cAMP levels measured as described above. Basal levels of cAMP were less than 10 pmol/$10^6$ cells in the absence of forskolin. Total cellular cAMP levels rose to over 170 pmol/$10^6$ cells in the presence of 100 μM forskolin.

Example 3

Direct Measurement of Intracellular Interleukin-6 by Enzyme-Linked Immunosorbent Assay This experiment describes a simple and direct method for the measurement of intracellular levels of Interleukin-6 (a cytokine). Unlike the previous examples for cAMP, the method described here is a two-stage process whereby cells are cultured, stimulated and lysed on a conventional tissue plate, and an aliquot of lysate is transferred to a second plate for assay.

Endothelial cells were stimulated with Interleukin-1β (IL-1β) overnight and lysed with DTAB. The lysate was analysed for the presence of Interleukin-6 (IL-6) by ELISA. The critical component of the ELISA (the biotinylated antibody) was prepared in buffer containing the sequestrant (3% w/v alpha-cyclodextrin). The method is quick, easy and sensitive enough to require only a few cells (<$10^5$) per well.

Reagents, Buffers and Equipment
1) Human Interleukin-6 ELISA kit, Amersham, RPN 2754
2) Alpha-cyclodextrin, USB, 13979
3) DTAB, Sigma, D8638
4) IL-1β, Amersham, ARM 17005
5) ECV304 cells, a human endothelial cell line derived from a new-born Japanese female.

Additional materials and equipment are as follows.
a) Standard 96-well tissue culture plates
b) Disposable test tubes for preparing working standards
c) Pipettes and pipetting equipment
d) Laboratory glassware
e) Distilled water
f) Vortex mixer
g) Magnetic stirrer
h) 1% (w/v) trypan blue solution prepared in water
i) Haemocytometer
j) M-199 media, Sigma, M-7653
k) Microtitre plate washer
l) Microtitre plate reader Method ECV304 cells were cultured in M-199 media containing 10% (v/v) foetal calf sera (FCS). For IL-6 assays, cells were seeded into standard 96-well tissue culture plates in 100 μl volumes (between $10^5$–$10^6$ cells/ml). Cells were cultured overnight at 37° C. in a 95% air/5% $CO_2$ atmosphere. On day 2 working solutions of IL-1β (2–500 pg/ml; final concentration) were prepared in M-199 media in order to stimulate the production of IL-6. A culture media blank was prepared with cultured cells grown in the absence of IL-1β. Cells were again cultured overnight at 37° C. in a 95% air/5% $CO_2$ atmosphere. On day 3, a 1% (wt) solution of DTAB was prepared in standard diluent. This reagent was used to lyse the cells and for the preparation of working standards. After overnight incubation, the cell culture supernatants were decanted (the cells remain adhered to the surface of the culture vessel). The cells were gently washed X3 with phosphate buffered saline. After the third wash, the cells were checked to ensure none were lost. 100 μl of the lysis reagent (1% DTAB in standard diluent) was added to the cells. Cell lysis was checked with trypan blue exclusion.

Working standards (10.24400 pg/ml IL-6) were prepared in polypropylene tubes using assay buffer containing 1% (w/v) DTAB. The biotinylated antibody was prepared in buffer containing 3% (w/v) alpha-cyclodextrin. 50 μl of biotinylated antibody (containing cyclodextrin) was added to the anti-IL-6 coated plate. 50 μl of working standard and cell lysate was pipetted into separate wells of the anti-IL-6 coated plate. Non-specific binding was measured in the absence of IL-6 (zero IL-6 standard). The order of addition of biotinylated antibody and samples/standards is not critical to the procedure. However, in this example, improved results were obtained when the biotinylated antibody was added to the anti-IL-6 coated plate before the standards or samples. The anti-IL-6 plate, containing biotinylated antibody and standards/samples, was incubated for 2 hours at room temperature. The plate was washed thoroughly, followed by the addition of 100 μl/well of diluted (30 μl of concentrate to 12 ml of streptavidin dilution buffer) peroxidase-labelled streptavidin. The plate was incubated at room temperature for 30 minutes followed by thorough washing. 100 μl of TMB substrate was added to each well of the plate, followed by a 30 minute incubation at room temperature. The reaction was terminated by the addition of 100 μl/well sulphuric acid. The optical density was determined with a microtitre plate spectrophotometer set at 450 nm. Interleukin-6 levels were determined using log/linear analysis with reference to a standard curve. Levels were estimated by interpolation.

Results

Figure 5:
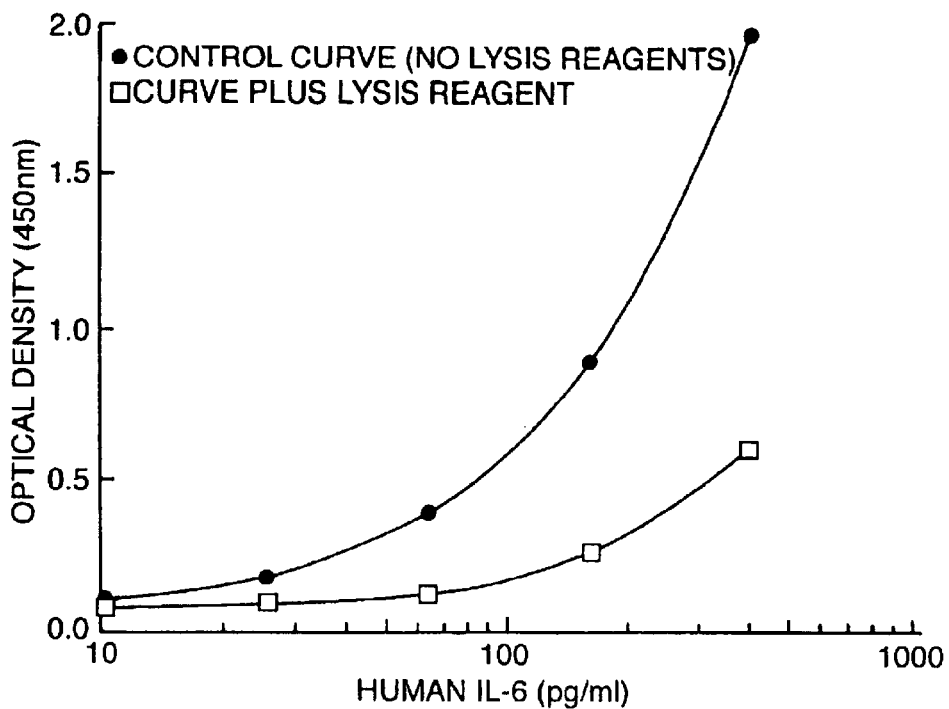
FIG. 5. Inhibition of binding in the IL-6 ELISA with lysis reagent.
Figure 6:
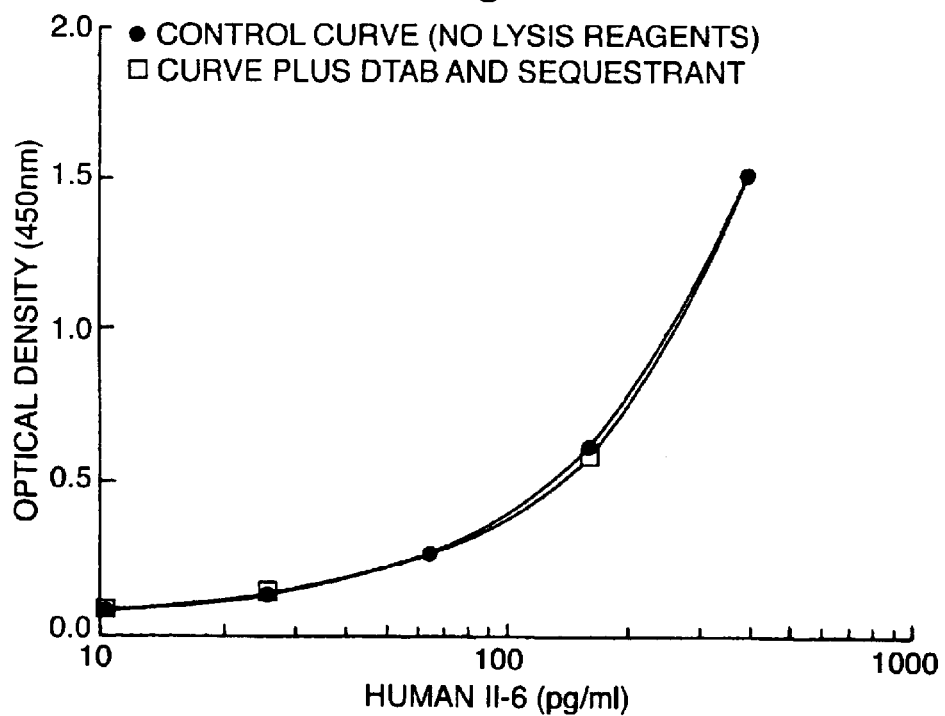
FIG. 6. Restoration of binding in the IL-6 ELISA with sequestrant.

The effect of including lysis reagent and sequestrant on the IL-6 ELISA system is presented in FIGS. 5 & 6. FIG. 5 shows an inhibition of antibody binding when 1% DTAB is added to the IL-6 assay. Binding was restored upon the addition of 3% (w/v) alpha-cyclodextrin (FIG. 6). The results of stimulating ECV304 cells with IL-1β, and the measurement of intracellular IL-6 is shown in FIG. 7. Basal levels of IL-6 were less than 30 pg/$10^6$ cells in the absence of IL-β. Intracellular IL-6 levels rose to over 400 pg/$10^6$ cells in the presence of 500 pg/ml IL-1β.

Example 4

Measurement of "Total" Cellular Interleukin-6 from IL-1β Stimulated ECV304 Cells This experiment describes a method for measurement of "total" cellular Interleukin-6. The procedure is applicable to cell culture systems and is suitable for the measurement of molecules (such as cytokines) that are secreted into cell culture fluids.

Reagents, Buffers and Equipment
1) Human Interleukin-6 ELISA kit, Amersham, RPN 2754
2) Alpha-cyclodextrin, USB, 13979
2) DTAB, Sigma, D8638
3) IL-1β, Amersham, ARM 17005
4) ECV 304 cells, a human endothelial cell line derived from a new-born Japanese female.

Additional materials and equipment are as follows.
a) Standard 96-well tissue culture plates
b) Disposable test tubes for preparing working standards
c) Pipettes and pipetting equipment
d) Laboratory glassware
e) Distilled water
f) Vortex mixer
g) Magnetic stirrer
h) 1% (w/v) trypan blue solution prepared in water
i) Haemocytometer
j) M-199 media
k) Microtitre plate washer
l) Microtitre plate reader Method ECV304 cells were cultured in M-199 media containing 10% (v/v) foetal calf sera (FCS). For IL-6 assays, cells were seeded into standard 96-well tissue culture plates in 100 µl volumes (between $10^5$–$10^5$ cells/ml). Cells were cultured overnight at 37° C. in a 95% air/5% $CO_2$ atmosphere. On day 2, working solutions of IL-1β (2–500 pg/ml, final concentration) were prepared in M-199 media in order to stimulate the production of IL-6. A culture media blank was prepared with cells in the absence of IL-1β. Cells were again cultured overnight at 37° C. in a 95% air/5% $CO_2$ atmosphere. On day 3, sequestration and lysis buffers (3% alpha-cyclodextrin, 1% and 10% DTAB) were prepared. The lysis reagents were prepared in standard diluent. The 10% DTAB solution was used for cell lysis, the 1% DTAB solution for the preparation of working standards.

10 µl of cell lysis reagent (10% DTAB) were added to the stimulated cells. The cells were agitated and the plate incubated for 5 minutes at room temperature. The final volume in the wells was 110 µl. Cellular lysis was checked with trypan blue exclusion. The "total" cellular IL-6 was measured immediately with ELISA.

Working standards (10.24–400 pg/ml IL-6) were prepared in polypropylene tubes with assay buffer containing 1% (w/v) DTAB. The biotinylated antibody was prepared in buffer containing 3% (w/v) alpha-cyclodextrin. 50 µl of biotinylated antibody (containing cyclodextrin) was added to an anti-IL-6 coated plate. 50 µl of working standard and "total" cell lysate was pipetted into separate wells of the anti-IL-6 coated plate. Non-specific binding was measured in the absence of IL-6 (zero IL-6 standard). The order of addition of biotinylated antibody and samples/standards is not critical to the procedure. However, in this example, improved results were obtained when the biotinylated antibody was added to the anti-IL-6 coated plate before the standards or samples. The anti-IL-6 plate, containing biotinylated antibody standards and samples, was incubated for 2 hours at room temperature. The plate was washed thoroughly, followed by the addition of 100 µl/well of diluted (30 µl of concentrate added to 12 ml of streptavidin dilution buffer) peroxidase-labelled streptavidin. The plate was incubated at room temperature for 30 minutes followed by thorough washing. One hundred microliters of TMB substrate was added to each well, followed by a 30 minute incubation at room temperature. The reaction was terminated by the addition of 100 µl/well sulphuric acid. The optical density was determined in each well with a microtitre plate spectrophotometer set at 450 nm. Total cellular Interleukin-6 levels were determined using log/linear analysis with reference to the standard curve. Levels were estimated by interpolation.

Results

The effect of stimulation of ECV304 cells with IL-1β, and the measurement of intracellular, total cellular, and IL-6 measured in the cell culture supernatant, is presented in FIG. 8. Compared with the cell culture supernatant, significantly higher levels of IL-6 was measured in the "total" lysate fraction.

Experiment 5: Radioreceptor Binding Assay for D-myo-inositol 1,4,5-trisphosphate ($IP_3$)

1. Established methods for preparing cells for measurement of inositol 1,4,5-trisphosphate ($IP_3$) include acid extraction procedures, processes which require careful neutralisation with alkali before assay. The technique described here is based on competition of [$^3$H] inositol 1,4,5-trisphosphate (the tracer) with unlabelled $IP_3$ in the sample or standard to a binding protein prepared from bovine adrenal cortex. As in previous experiments, DTAB is used as a lysis reagent and alpha-cyclodextrin as the sequestrant. Clearly, the method is applicable to the intracellular measurement of $IP_3$, and has a number of advantages over traditional techniques for $IP_3$ extraction before to assay.

Reagents, Buffers and Equipment

1. D-myo-inositol 1,4,5-trisphosphate ($IP_3$) Radioreceptor kit, Amersham, TRK1000
2. 2) Alpha-cyclodextrin, USB, 13979
3. 3) DTAB, Sigma, D8638
4. 4) 10% (v/v) acetic acid
5. 5) 0.15M sodium hydroxide Additional materials and equipment required are as follows.

a) Pipettes and pipetting equipment
b) Polypropylene test tubes
c) Distilled water
d) Vortex mixer
e) Refrigerated centrifuge
f) β-scintillation counter
g) Scintillant
h) Counting vials
i) Ice bath
j) Decantation racks Method Bovine adrenal glands were removed from animals and stored at −20° C. before preparing the binding protein. The cortex was dissected from the adrenal glands, homogenised in $NaHCO_3$ (20 mM) with dithiothreitol (1 mM), and the homogenate centrifuged at 5000 g for 15 minutes. The supernatant was centrifuged at 35000 g for 20 minutes, the resulting pellet resuspended in the homogenisation buffer and centrifuged again at 35000 g for 20 minutes. The final pellet was resuspended in homogenisaton buffer at a protein concentration of between 20–40 mg/ml.

For the assay, aliquots (100 µl) of the bovine adrenal cortex microsome preparation were incubated in 100 µl of 0.1M Tris buffer (pH9.0), containing 4 mM EDTA and 4 mg/ml bovine serum albumin. Incubations were carried out for 15 minutes in a final volume of 0.4 ml with [$^3$H] inositol 1,4,5-trisphosphate (100 µl; 6000 cpm) sample or standard (100 µl; 0.19–25 pmol inositol 1,4,5-trisphosphate/assay tube). Non-specific binding was determined in the presence of 1 nmol inositol 1,4,5-trisphosphate/tube. Incubations were terminated by centrifugation (12000 g) (10 minutes at 4° C.) and removal of the supernatant by gentle decantation. Particulate bound radioactivity was analysed, after suspension in 0.15M sodium hydroxide followed by neutralisation with 10% acetic acid, by liquid scintillation counting Experiments were set up with:—
1) Working standards (0.19–25 pmol $IP_3$/tube) were prepared in water (control) or, in water containing lysis reagent (0.5% w/v).
2) The binding protein, prepared as above (control) or, in homogenisation buffer containing 2% (w/v) alpha-cyclodextrin.
3) Radioactive tracer prepared in water (control) or, in water containing 2% (w/v) alpha-cyclodextrin.

Results

Figure 9:
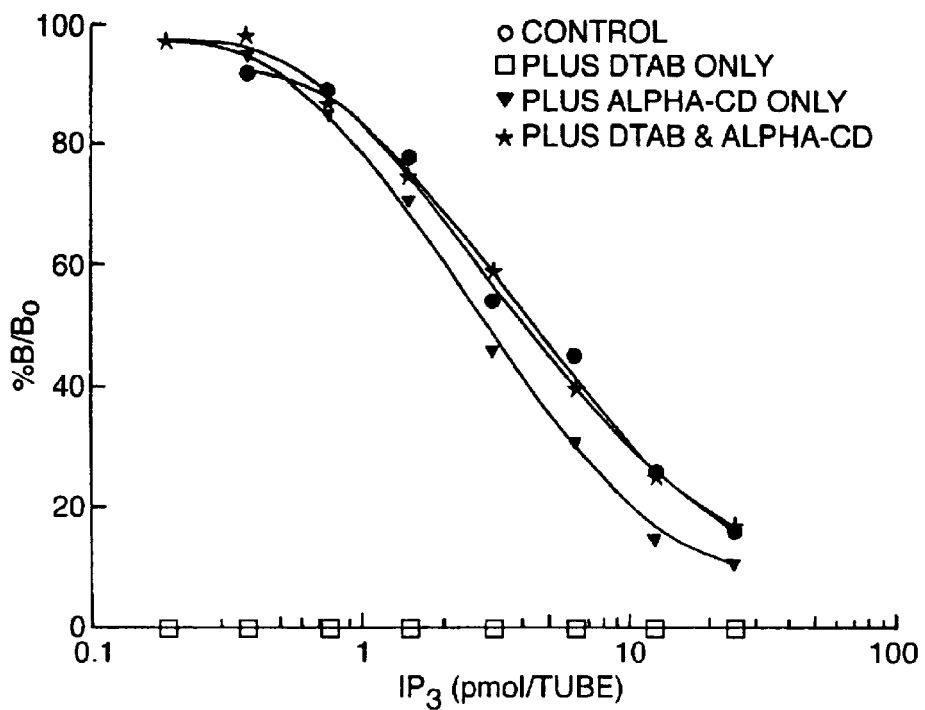
FIG. 9. Standard curves for the IP: radioreceptor assay.

The effect of adding lysis reagent to the $IP_3$ standards and sequestrant to the tracer and binding protein is shown in FIG. 9. In standard curves where lysis reagent (0.5% w/v DTAB) was included, there was a total inhibition of binding to the receptor preparation. Binding was restored when alpha-cyclodextrin (2% final w/v) was added to both the tracer and the adrenal cortex preparation.

Example 5

Direct Measurement of Intracellular Prostaglandin $E_2$ in Mouse 3T3 Cells

This experiment describes a simple and convenient method for the direct measurement of intracellular levels of prostaglandin $E_2$ from stimulated Mouse Swiss 3T3 Albino embryo fibroblast cells. Prostaglandin $E_2$ ($PGE_2$) is a product of arachidonic acid metabolism and the cyclooxygenase pathway. The method described here involves a two-stage process where cells are cultured, stimulated and lysed on a conventional tissue-culture plate and an aliquot of lysate is transferred to a second plate for measurement with a competitive enzymeimmunoassay (EIA) technique. Mouse 3T3 cells were stimulated with the calcium ionophore A23187 for 5 minutes, washed, and lysed with DTAB. The lysate was analysed for the presence of $PGE_2$ with EIA. The critical components of the assay (the $PGE_2$ peroxidase conjugate and the $PGE_2$ antiserum) were prepared in buffer containing the sequestrant (2.5% alpha-cyclodextrin). The method is very quick, easy to carry out and sensitive enough to require only a few cells ($<10^5$) per well.

Reagents, buffers and equipment
1. Prostaglandin $E_2$ enzymeimmunoassay (EIA) kit, Amersham, RPN 222
2. Alpha-cyclodextrin, USB, 13979
3. DTAB, Sigma, D-8638
4. Calcium ionophore A23187, Sigma, C-7522
5. Mouse 3T3 cells, ECACC
6. DMEM media, Sigma, D546

Additional materials and equipment are as follows:—
a) Standard 96-well tissue culture plates
b) Disposable test tubes for preparing working standards
c) Pipettes and pipetting equipment
d) Laboratory glassware
e) Distilled water
f) Vortex mixer
g) Magnetic stirrer
h) 1% (w/v) Trypan blue solution prepared in water
i) Haemocytometer
j) Microtitre plate washer
k) Microtitre plate reader Method Mouse 3T3 cells were cultured in DMEM media containing 10% (v/v) foetal calf sera (FCS). For $PGE_2$ assays, cells were seeded into standard 96-well tissue culture plates in 100 µl volumes (between $10^5$–$10^6$ cells/ml). Cells were cultured overnight at 37° C. in a 95% air/5% $CO_2$ atmosphere. At this stage a check was made to ensure cells remained viable with Trypan blue exclusion.

On day 2, working solutions of A23187 (1–100 µM final concentration) were prepared in DMEM media in order to stimulate the production of $PGE_2$. Two controls were prepared (a DMSO and a culture media only control). Here cells were cultured in the absence of A23187. Test cell cultures were stimulated with the calcium ionophore A23187 for 5 minutes at room temperature. The culture supernatant was decanted, cells were washed with phosphate buffered saline and lysed with 100 µl/well 0.5% (w/v) DTAB prepared in assay buffer. A check for cell lysis was made with a second Trypan blue exclusion test.

Working $PGE_2$ standards (2.5–320 pg/well) were prepared in polypropylene tubes with assay buffer containing 0.5% (w/v) DTAB. The $PGE_2$ antibody and $PGE_2$ conjugate were prepared with assay buffer containing 2.5% (w/v) alpha-cyclodextrin. 50 µl of working standard and cell lysate were pipetted into separate wells of a goat anti-mouse IgG coated plate. Non-specific binding was measured in the absence of $PGE_2$ antisera. Zero standard $PGE_2$ consisted of assay buffer containing 0.5% (w/v) DTAB only. 50 µl of antisera and 50 µl conjugate (prepared in assay buffer containing 2.5% (w/v) alpha-cyclodextrin) were pipetted into the appropriate test wells (containing standards and sample cell lysates). The plates were incubated for 1 hour at room temperature with constant shaking, followed by thorough washing. 150 µl of TMB substrate was added to all wells and incubated for 30 minutes at room temperature. The reaction was terminated by the addition of 100 µl/well sulphuric acid. The optical densities were determined with a microtitre plate spectrophotometer set at 450 nm. Intracellular $PGE_2$ levels were determined using log/linear analysis with reference to a standard curve. Levels were estimated by interpolation.

Results

Figure 10:
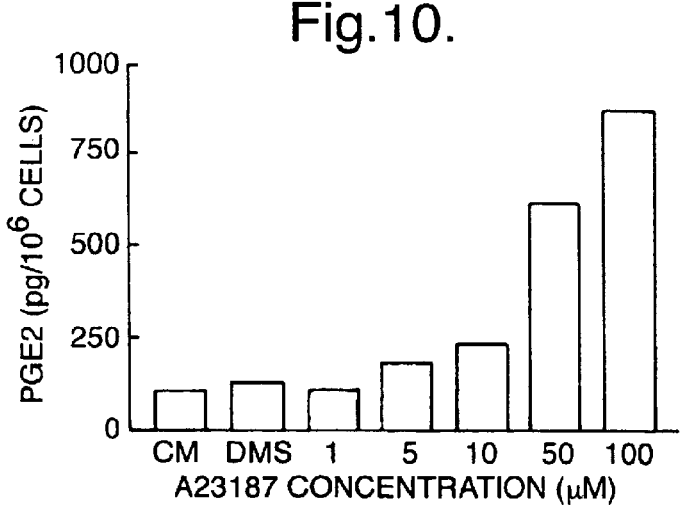
FIG. 10. Intracellular PGEZ measurement from 3T3 cells.

The results of stimulating 3T3 cells with the calcium ionophore A23187, and the direct measurement of intracellular $PGE_2$ are shown in FIG. 10. Basal levels of $PGE_2$ were approximately 50 pg/$10^6$ cells in the absence of A23187. Intracellular $PGE_2$ levels rose to over 400 pg/$10^6$ cells in the presence of 100 µM A23187.

Legend to Figures

FIG. 1. Representative Standard Curve for the Concerted One-Pot Extraction and Immunoassay Method for the Estimation of Adenosine 3'5' Cyclic Monophosphate from Cultured Chinese Hamster Ovary Cells.

Assay curves were prepared on Viewplates (Packard) as described in the methods section.

The percent $B/B_0$ function was calculated from the following formula:—

[(standard counts per minute)-(non-specific binding counts per minute)] divided by [(zero standard counts per minute)-(non-specific binding counts per minute)] multiplied by 100%.

Typically, counts per minute values for the zero dose were 2200. The counts per minute values obtained in the absence of specific antibody (non-specific binding wells) were approximately 200. The values in the absence of tracer were usually less than 25 cpm.

Figure 2:
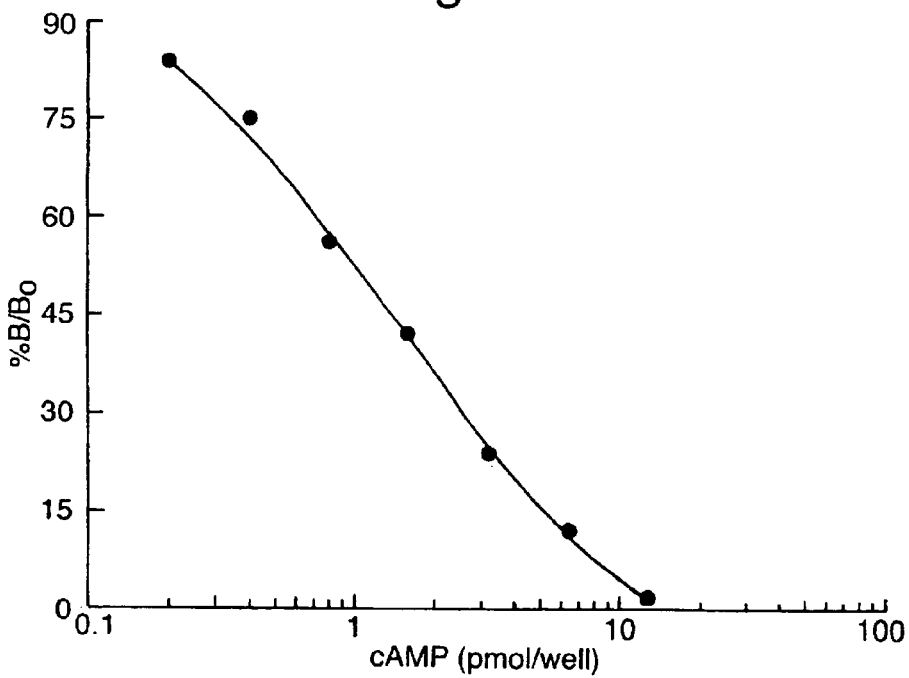
FIG. 2. Representative standard curve for the concerted one-pot extraction and immunoassay method for the estimation of adenosine 3'5' cyclic monophosphate from cultured Chinese Hamster Ovary cells. Assay curves were prepared on Cytostar-T described in the methods section.

FIG. 2. Representative Standard Curve for the Concerted One-Pot Extraction and Immunoassay Method for the Estimation of Adenosine 3'5' Cyclic Monophosphate from Cultured Chinese Hamster Ovary Cells.

Assay curves were prepared on Cytostar-T as described in the methods section.

The percent $B/B_0$ function was calculated from the following formula:—

[(standard counts per minute)-(non-specific binding counts per minute)] divided by [(zero standard counts per minute)-(nonspecific binding counts per minute)] multiplied by 100%.

Typically, counts per minute values for the zero dose were 2200. The counts per minute values obtained in the absence of specific antibody (non-specific binding wells) were approximately 200. The values in the absence of tracer were usually less than 25 cpm.

FIG. 3. Forskolin-Stimulated cAMP Generation from Cultured Chinese Hamster Ovary Cells as Determined by the One-Pot Extraction SPA Radioimmunoassay Method.

CHO cells were seeded at a density of 100,000 cells per well and grown overnight to confluence in clear-bottomed Cytostar-T or Viewplates as described under the methods section. Cells were exposed to various concentrations of forskolin and cAMP extracted and levels determined with the SPA radioimmuunoassay procedure. Basal levels of cAMP were less than 10 pmoles/$10^6$ cells which significantly increased on stimulation by forskolin.

FIG. 4. "Total" Cellular cAMP Measurement from Cultured Chinese Hamster Ovary Cells Chinese hamster ovary cells were seeded at a density of 100,000 cells per well and cultured overnight to confluence in Viewplates as described under the methods section. Cells were exposed to various concentrations of forskolin (1 $\mu$M–100 $\mu$M) for 20 minutes at room temperature. Cells were lysed in situ by addition of lysis reagent (10% DTAB added, 1% final concentration). The cell culture supernatant was not removed before the cell lysis step. cAMP levels were measured with the SPA radioimmunoassay procedure. Basal levels of cAMP were less than 10 pmoles/$10^6$ cells, total cellular cAMP levels rose significantly when cells were stimulated with forskolin.

FIG. 5. Inhibition of Binding in the IL-6 ELISA with Lysis Reagent

Interleukin-6 standards (10.24–400 pg/ml) were prepared in standard diluent either in the presence (□) or absence (●) of lysis reagent (1% w/v DTAB). Aliquots (50 $\mu$l) of biotinylated antibody (zero cyclodextrin), were added to the anti-IL-6 coated plate followed by standard (50 $\mu$l). The plate was incubated for 2 hours at room temperature, and the optical density measured as described under the methods section.

FIG. 6. Restoration of Binding in the IL-6 ELISA with Sequestrant

Interleukin-6 standards (10.24–400 pg/ml) were prepared in standard diluent either in the presence (□) or absence (●) of lysis reagent (1% w/v DTAB). Aliquots (50 $\mu$l) of biotinylated antibody, prepared in the presence (□) or absence (●) of cyclodextrin (3% w/v), were added to the anti-IL-6 coated plate followed by standard (50 $\mu$l). The plate was incubated for 2 hours at room temperature, and the optical density measured as described under the methods section.

FIG. 7. Intracellular Measurement of IL-6 from IL-1$\beta$ Stimulated ECV304 Cells ECV304 cells were seeded at a density of 100,000 cells per well and cultured overnight to confluence in standard 96-well tissue culture plates as described under the methods section. Cells were exposed to various concentrations of IL-1$\beta$ (2–500 pg/ml) overnight and the supernatant decanted. The cells were washed thoroughly and 100 $\mu$l of lysis reagent (1% DTAB) added. Aliquots (50 $\mu$l) of cell lysate were transferred to a second 96-well plate coated with anti-IL-6 antibody for assay. Levels of IL-6 were measured in the samples with ELISA (the biotinylated antibody was prepared in the presence of 3% (w/v) alpha-cyclodextrin).

FIG. 8. Interleukin-6 Measurement from ECV304 Cells

ECV304 cells were seeded at a density of 100,000 cells per well and cultured overnight to confluence in standard 96-well tissue culture plates as described under the methods section. Cells were exposed to IL-1$\beta$ overnight and IL-6 measured in the intracellular fraction (see experiment 7), cell culture supernatant (with a traditional ELISA technique), and in the "total" cellular fraction. For the total cellular assay, cells were lysed in situ by addition of lysis reagent (10% DTAB added, 1% final concentration). The cell culture supernatant was not removed before the cell lysis step. Aliquots (50 $\mu$l) of 'total' cellular lysate were transferred to a second 96-well plate coated with anti-IL-6 antibody for assay. Levels of ILL were measured in the samples with ELISA (the biotinylated antibody was prepared in the presence of 3% (w/v) alpha-cyclodextrin).

FIG. 9. Standard Curves for the $IP_3$ Radioreceptor Assay

Increasing concentrations of inositol 1,4,5-trisphosphate were allowed to compete with [$^3$H] inositol 1,4,5-trisphosphate for binding to the bovine adrenal cortex binding protein for 15 minutes at 4° C. Curves were prepared in the absence of both lysis reagent and sequestrant (control, ●), with lysis reagent only (□), with sequestrant only (♥), and with both lysis reagent and sequestrant (☆). The lysis reagent totally inhibited specific binding to the receptor preparation. Binding was restored when tracer and binding protein were prepared with sequestrant.

FIG. 10. Intracellular $PGE_2$ Measurement from 3T3 Cells

3T3 cells were seeded at a density of 100,000 cells per well and cultured overnight to confluence in standard 96-well tissue culture A; plates as described under the methods section. Cells were exposed to various concentrations of calcium ionophore A23187 (1–100 $\mu$M) for 5 minutes, and the supernatant decanted. The cells were washed thoroughly and 100 $\mu$l of lysis reagent (0.5% DTAB) added. Aliquots (50 $\mu$l) of cell lysate were transferred to a second 96-well plate coated with goat anti-mouse IgG for assay. The lysate was analysed for the presence of ($PGE_2$ by EIA. The critical components of the assay (the $PGE_2$ peroxidase conjugate and the $PGE_2$ antiserum) were prepared in buffer containing the sequestrant (2.5% alpha-cyclodextrin).

What is claimed is:

1. An improved method of conducting a specific binding assay for the presence of an intracellular analyte in a cultured cell sample which method comprises the steps of:
   i) mixing a sample of cultured cells with a cell lysis reagent to provide a lysed cellular sample;
   ii) mixing and reacting the lysed cellular sample with a specific binding assay reagent comprising a specific binding partner of the intracellular analyte and a tracer to perform a specific binding assay; thus forming a reaction mixture comprising a specific-binding partner-intracellular analyte complex;
   iii) mixing the lysed cellular sample with a cyclodextrin sequestrant for the cell lysis reagent, whereby the specific binding assay of step ii) is performed in the presence of the sequestrant; and
   iv) detecting the presence of the specific binding partner-intracellular analyte complex, the presence of which is indicative of the presence of intracellular analyte in the sample wherein the improvement lies in adding the sequestrant in the amount of 0.5–10% by weight based on the weight of the reaction mixture.

2. The method as claimed in claim 1, wherein the cell lysis reagent is a detergent.

3. The method as claimed in claim 1, wherein the amount of cyclodextrin sequestrant is in the range of 1–5% of the said reaction mixture.

4. A method as claimed in claim 1, wherein steps i), ii) and iii) are all performed in a single reaction vessel.

5. A method of claimed in claim 1, wherein multiple assays are performed in parallel in wells of a multiwell plate.

6. A method as claimed in claim 1, wherein the cells are cultured in a vessel and are lysed in that vessel for assaying the analyte in that vessel.

7. A method as claimed in claim 1, wherein the assay of step ii) is a homogenous assay.

8. A method as claimed in claim 1, wherein the assay of step ii) is a homogenous assay.

9. A method as claimed in claim 1, wherein the specific binding assay of step ii) is an immunoassay.

10. A method as claimed in claim 1, wherein the analyte is adenosine-3', 5'-cyclic monophosphate, the cell lysis reagent is dodecyl trimethyl ammonium bromide and the sequestrant is α-cyclodextrin.

11. A method as claimed in claim 1, wherein the cells have been maintained in a culture medium, and step i) is performed in the presence of the culture medium.

12. A method as claimed in claim 1, wherein the intracellular or intracellular plus extracellular concentration is measured of an analyte selected from adenosine-3', 5'-cyclic monophosphate, interleukin-6 and prostaglandin $E_2$.

13. The method as claimed in claim 1, wherein the specific binding assay is a receptor binding assay.

14. The method as claimed in claim 1, which further comprises the step of separating bound tracer from unbound tracer.

15. The method as claimed in claim 1, wherein the tracer is selected from the group consisting of radioactive isotope label, enzyme-linked label and fluorescent label.

16. A method as claimed in claim 1, wherein the specific binding assay of step ii) is a fluorescence a polarization immunoassay.

* * * * *

UNITED STATES PATENT AND TRADEMARK OFFICE
CERTIFICATE OF CORRECTION

PATENT NO. : 6,900,019 B1
DATED : May 31, 2005
INVENTOR(S) : Jeffrey K. Horton

It is certified that error appears in the above-identified patent and that said Letters Patent is hereby corrected as shown below:

<u>Column 30,</u>
Line 8, after "binding assay of step ii) is" please delete "fluorescence a polarization" and insert -- fluorescence polarization -- in its place.

Signed and Sealed this

Thirtieth Day of August, 2005

JON W. DUDAS
*Director of the United States Patent and Trademark Office*